US010086082B2

(12) United States Patent
Davidson et al.

(10) Patent No.: US 10,086,082 B2
(45) Date of Patent: Oct. 2, 2018

(54) PLANT STEROIDS AND USES THEREOF

(75) Inventors: Michael Davidson, Highland Park, IL (US); John F. Arnett, Millstone Township, NJ (US); Sadik Elshani, Philadelphia, PA (US); Roelof Rongen, Califon, NJ (US)

(73) Assignee: DAVIDSON LOPEZ LLC, Highland Park, IL (US)

( * ) Notice: Subject to any disclaimer, the term of this patent is extended or adjusted under 35 U.S.C. 154(b) by 221 days.

(21) Appl. No.: 14/345,028

(22) PCT Filed: Sep. 14, 2012

(86) PCT No.: PCT/US2012/055549
§ 371 (c)(1),
(2), (4) Date: Dec. 23, 2014

(87) PCT Pub. No.: WO2013/040441
PCT Pub. Date: Mar. 21, 2013

(65) Prior Publication Data
US 2015/0141390 A1    May 21, 2015

Related U.S. Application Data

(60) Provisional application No. 61/675,966, filed on Jul. 26, 2012, provisional application No. 61/535,661, filed on Sep. 16, 2011.

(51) Int. Cl.
*A61K 31/48*        (2006.01)
*A61K 31/573*       (2006.01)
(Continued)

(52) U.S. Cl.
CPC ...... *A61K 47/48123* (2013.01); *A61K 31/573* (2013.01); *A61K 31/575* (2013.01);
(Continued)

(58) Field of Classification Search
CPC .............. C07J 31/006; C07J 41/0055; A61K 47/48123; A61K 31/573; A61K 31/574
(Continued)

(56) References Cited

U.S. PATENT DOCUMENTS 8,188,060 B2 *   5/2012   Khvorova ............. C12N 15/111
                                              514/44 A
8,252,755 B2 *   8/2012   Yamada ................. C07H 19/00
                                              514/44 A
(Continued)

FOREIGN PATENT DOCUMENTS

WO          00/52029 A1      9/2000
WO          2002072035  *    9/2002
(Continued)

OTHER PUBLICATIONS

Hugh E. Black (The effects of steroid upon the Gastrointestinal Tract, Toxicologic Pathology ISSN:912-6233, vol. 16, No. 2, 1988).*
(Continued)

*Primary Examiner* — Sabiha N Qazi
(74) *Attorney, Agent, or Firm* — Polsinelli PC; Ron Galant

(57) ABSTRACT

The invention relates to a drug conjugate including a drug and a plant steroid. The drug conjugate may target the drug for intestinal cell delivery, and thus may be used to treat diseases, including intestinal diseases, or to affect intestinal metabolism. The invention therefore also relates to treating intestinal diseases and affecting intestinal metabolism with the drug conjugate.

11 Claims, 36 Drawing Sheets

Phytosterols/stanols to deliver drugs to intestinal cells

Redrawn and modified from SEHAYEK E J Lipid Res 44:2030, 2003

(51) Int. Cl.
A61K 31/575 (2006.01)
A61K 47/48 (2006.01)
C07J 9/00 (2006.01)
C07J 41/00 (2006.01)
C07J 71/00 (2006.01)
A61K 47/54 (2017.01)
C07J 31/00 (2006.01)

(52) U.S. Cl.
CPC ............... *A61K 47/554* (2017.08); *C07J 9/00* (2013.01); *C07J 41/0055* (2013.01); *C07J 71/0031* (2013.01); *C07J 31/006* (2013.01)

(58) Field of Classification Search
USPC .......................................... 514/182; 552/509
See application file for complete search history.

(56) References Cited

U.S. PATENT DOCUMENTS

| | | | | |
|---|---|---|---|---|
| 8,415,466 | B2* | 4/2013 | Khvorova | C12N 15/111 536/24.1 |
| 2004/0152663 | A1 | 8/2004 | Byun et al. | |
| 2004/0236125 | A1* | 11/2004 | Kutney | A61K 31/575 552/508 |
| 2005/0234025 | A1* | 10/2005 | Kutney | A61K 31/045 514/171 |
| 2009/0110633 | A1* | 4/2009 | Sengupta | A61K 9/1271 424/1.29 |

FOREIGN PATENT DOCUMENTS

| | | |
|---|---|---|
| WO | 2004/095926 A2 | 11/2004 |
| WO | 2008/036825 A2 | 3/2008 |
| WO | 2011/109472 A1 | 9/2011 |

OTHER PUBLICATIONS

Svobodova et al. (Journal of colloidal and Interface Science 361 (2011) 587-594).*
Yano et al. (Journal of controlled release, 79 (2002) 103-112).*
Habiger, R.G., et al., "Influence of stigmastanol and stigmastanylphosphorylcholine, two plasma cholesterol lowering substances, on synthetic phospholipid membranes," Biochimica ET Biophysica Acta (BBA)—Biomembranes, Elsevier, Amsterdam, NL, vol. 1103, No. 1, Jan. 10, 1992, pp. 69-76.
Extended Supplementary European Search Report, European Patent Application No. 12832645.1, dated Jan. 29, 2015 nine pages.
Marquet, F., et al., "Selection of cholesterol absorption inhibitors devoid of secondary intestinal effects," Reproduction Nutrition Development, EDP Sciences, 1997, 37(6), pp. 691-707.
Yano, H., et al., "Colon-specific delivery of prednisolone-appended alpha-cyclodextrin conjugate; alleviation of systemic side effect after oral administration," Journal of Controlled Release, Elsevier, Amsterdam, NL, vol. 79, No. 1-3, Feb. 19, 2002, pp. 103-112.
J. Plat: "Plant sterols and stanols: effects on mixed micellar composition and LXR (target gene) activation," The Journal of Lipid Research, vol. 46, No. 11, Sep. 8, 2005, pp. 2468-2476.
Behrman, E.J., et al., "Cholesterol and Plants," Journal of Chemical Education, vol. 82, No. 12, Dec. 1, 2005, pp. 1791-1793, XP55310621.
Horibe, S., et al., "Preventative Effects of Sodium Alginate on Indomethacin-induced Small-intestinal Injury in Mice," International Journal of Medical Sciences, vol. 13, No. 9, Jan. 1, 2016, pp. 653-663, XP55311200.
Relja, B., et al., "Pre-or post-treatment with ethanol and ethyl pyruvate results in distinct anti-inflammatory responses of human lung epithelial cells triggered by interleukin-6", Molecular Medicine Reports, May 8, 2015, XP55310712.
Young, et al., "The anti-inflammatory effects of heparin and related compounds," Thrombosis Research, Tarrytown, NY, US, vol. 122, No. 6, Jan. 1, 2008, pp. 743-752, XP025466363.
Rowley, T.J., et al., "Antinociceptive and anti-inflammatory effects of choline in a mouse model of postoperative pain," British Journal of Anaesthesia, vol. 105, No. 2, Aug. 1, 2010, pp. 201-207, XP055310789.
Fuchs, J., et al., "Modulation of uv-light-induced skin inflammation by Dalpha-tocopherol and L-ascorbic acid: A clinical study using solar simulated radiation," Free Radical Biology and Medicine, Elsevier Inc., US, vol. 25, No. 9, Dec. 1, 1998, pp. 1006-1012, XP002283436.
Chaiyotwittayakun, A., et al., "The Effect of Ascorbic Acid and I-Histidine Therapy on Acute Mammary Inflammation in Dairy Cattle," Journal of Dairy Science, American Dairy Science Association, US, vol. 85, No. 1, Jan. 1, 2002, pp. 60-67, XP026990514.
Hu, N., et al. "HMGB1 Silencing Potentiates the Anti-inflammatory Effects of Sodium Ferulate in ox-LDL-Stimulated Vascular Smooth Muscle Cells," Cell Biochemistry and Biophysics, vol. 72, No. 1, Jan. 6, 2015, pp. 297-304, XP055310962.
Aparna, V., et al., "Anti-inflammatory property of n-hexadecanoic acid: structural evidence and kinetic assessment. PubMed—NCBI", Jan. 1, 2012, XP055311009.
Database CA [Online] Chemical Abstracts Service, Columbus, OH, US, Wakeham, S.G., et al., "Glass capillary gas chromatographymass spectrometry of wax esters, steryl esters and triacylglycerols," retrieved from STN Database accession No. 1983:68203.
W.D. Nes, Biosynthesis of Cholesterol and Other Sterols, Chem. Rev., vol. 111, pp. 6423-6451 (2011).
Y.S. Chhonker, et al., Assessment of an in vitro metabolic stability, plasma protein binding, and pharmacokinetics of E- and Z-guggulsterone in rat, Drug Test.Analysis, vol. 8, pp. 966-975, 971 (2016).

* cited by examiner

Phytosterols/stanols to deliver drugs to intestinal cells

Redrawn and modified from SEHAYEK E J Lipid Res 44:2030, 2003

FIGURE 3A

Genes affected from compound treatments (upregulation indicated in green, down regulation indicated in red)

| Regulated Genes | Treatments(Gene fold change for triplicate assays at 2.5 uM), n=3 | | | |
|---|---|---|---|---|
| | Prednisone | SE-22 | SE-24 | SE-41 |
| Tubulin beta | 4.2 | 3.1 | 2.75 | 1.2 |
| Keratin 18 | 4.4 | 7.1 | 7.7 | 1.4 |
| Low-density lipoprotein receptor | 6.7 | 3.3 | 4.23 | 1.3 |
| Insulin induced gene 1 | 10.3 | 14.4 | 13.3 | 1.5 |
| Anterior gradient 2 homolog (Xenopus laevis) | 3 | 6.2 | 1.2 | 1.97 |
| Keratin 8 | 5.5 | 4.3 | 2.5 | 1.8 |
| NAD(P) dependent steroid dehydrogenase-like | 3.1 | 3.3 | 5.45 | 1.1 |
| Tubulin, alpha, ubiquitous | 4.5 | 4.7 | 3.38 | 2 |
| Fatty acid synthase | 6.9 | 5.51 | 2.9 | 1.3 |
| Inhibitor of DNA binding 1 | 7.3 | 6.8 | 3.8 | 2.4 |
| Alpha-2-HS-glycoprotein | 4.2 | 4.4 | 6.4 | 1.1 |
| Apolipoprotein D | 8.9 | 7.4 | 6.8 | 2.2 |
| Wnt interacting factor | 7.6 | 4.5 | 4.5 | 1.3 |
| hepatocyte nuclear factor-4 NR2A1 | 6.4 | 10.7 | 6.6 | 1.2 |
| Zymogen granule protein 16 | 14 | 6.4 | 2.3 | 1.5 |
| Gamma-aminobutyric acid (GABA) A receptor, alpha 2 | 11.7 | 4.5 | 5.5 | 3.39 |
| Solute carrier family 36 member 1 | 15.3 | 3.5 | 4.3 | 3.5 |
| Calbindin D9K | 4.6 | 7.7 | 4.7 | 7.7 |
| Estrogen-like receptor, glucocorticoid receptor | 3.3 | 6 | 4.1 | 2.1 |
| RAR related orphan receptor NR1F2 | 4.6 | 3.2 | 3.4 | 1.3 |
| Soluble carrier family 1 member 1 | 3.1 | 3.2 | 3.71 | 1.6 |

FIGURE 3B

| | | | | |
|---|---|---|---|---|
| Alpha-fetoprotein | 7.7 | 9.7 | 1.3 | 4.1 |
| Apolipoprotein H | 5.5 | 2.3 | 3.4 | 1.34 |
| Fibrinogen, gamma polypeptide | 4.1 | 4.3 | 3.5 | 4.3 |
| Serine (or cysteine) proteinase inhibitor, clade A, member 6 | 6.9 | 5.2 | 3.6 | 3.1 |
| Transthyretin | 6.2 | 4.7 | 4.9 | 2.2 |
| Vitronectin | 4.4 | 6.6 | 4.2 | 2.3 |
| Inter-alpha (globulin) inhibitor, H2 polypeptide | 4.3 | 3.4 | 5.5 | 1.4 |
| Retinol binding protein 4 | 4.2 | 5.2 | 8.8 | 5.2 |
| Metallothionein 1F | 4.1 | 3.8 | 4.5 | 3.8 |
| Glypican 3 | 3.2 | 4.6 | 2.77 | 0 |
| Ornithine decarboxylase 1 | 3.1 | 3.5 | 2.76 | 0 |
| Heterogeneous nuclear ribonucleoprotein A3 | 3.5 | 3.4 | 2.4 | 2.17 |
| Human hepatic dihydrodiol dehydrogenase | 3.7 | 3.8 | 4.3 | 3.8 |
| Lipopolysaccharide-induced TNF factor | 3.1 | 2.4 | 5.97 | 4.4 |
| Hypothetical protein MAC | 3.1 | 2.1 | 1.4 | 3.2 |
| Liver receptor homolog 1, NR5A2 | 3.4 | 2.5 | 3.8 | 3.1 |
| Decay accelerating factor for complement (CD55, Cromer blood group system) | 3.3 | 1.4 | 7.7 | 5.5 |
| Vitamin D receptor NRI1 | 3.5 | 3.6 | 1.4 | 5.5 |
| Dual specificity phosphatase 1 | 3.2 | 3.7 | 4.3 | 0 |
| Phosphoenolpyruvate carboxykinase 1 (soluble) | 2.9 | 4.7 | 2.4 | 0 |
| Ras homolog gene family, member B | 3.4 | 4.88 | 4.1 | 3.1 |
| Apolipoprotein A-IV APOA4 | 3.3 | 3.4 | 3.9 | 0.97 |

FIGURE 3C

| | | | | |
|---|---|---|---|---|
| Dual specificity phosphatase 5 | 3.3 | 2.2 | 3.2 | 1.1 |
| Carcinoembryonic antigen-related molecule 1 (biliary glycoprotein) | 3.1 | 6.4 | 1.1 | 3.1 |
| Claudin 4 | 5.3 | 0 | 1.5 | 1.5 |
| Core promoter element binding protein | 3.1 | 2.4 | 1.2 | 1.4 |
| 3-Hydroxy-3-methylglutaryl-coenzyme A synthase 2 (mitochondrial) | 8.7 | 4.9 | 2.2 | 4.9 |
| Integrin, alpha 6 | 5.3 | 4.3 | 1.7 | 0 |
| Transmembrane 4 superfamily member 1 | 5.6 | 4.5 | 3.4 | 0 |
| Coagulation factor II (thrombin) receptor-like 1 | 7.3 | 4.5 | 1.3 | 0 |
| Uroplakin 1B | | | | |
| 3-Hydroxy-3-methylglutaryl-coenzyme A synthase 1 (soluble) | 4.4 | 3.7 | 3.9 | 1.4 |
| Insulin induced gene 1 | 4.7 | 3.2 | 1.2 | 1.32 |
| Syndecan binding protein (syntenin) | 4.4 | 3.7 | 2.6 | 1.7 |
| Annexin A 13 | 3.7 | 4 | 4.7 | 2.3 |
| Jun D proto-oncogene | 3.5 | 7 | 1.7 | 2.4 |
| Plasminogen activator, urokinase receptor | 3.1 | 5 | 3.4 | 3.23 |
| Cyclin-dependent kinase inhibitor 1C (p57, Kip2) | 3.1 | 6.3 | 4.1 | 2.25 |
| Retinoic acid induced 3 | 4.1 | 3.2 | 4.9 | 1.2 |
| Prostate differentiation factor | 3.2 | 3.4 | 1.66 | 1.1 |
| Tyrosine 3-monooxygenase/tryptophan 5-monooxygenase activation protein | 3.7 | 1.1 | 3.1 | 1.6 |

FIGURE 3D

| | | | | |
|---|---|---|---|---|
| Microsomal triglyceride transfer protein (large polypeptide, 88 kda) | 7.2 | 5.6 | 5.9 | 1.1 |
| Keratin 20 | 5.2 | 3.5 | 1.4 | 2.7 |
| Thymosin, beta 10 31481_s_at TMSB10 | 3.7 | 3.9 | 2.4 | 4.4 |
| Low-density lipoprotein receptor | 1.4 | 5.7 | 3.1 | 3.3 |
| Adipose differentiation-related protein | 4.9 | 6.6 | 1.3 | 2.6 |
| Apolipoprotein C-III | 4.6 | 3.3 | 2.2 | 2.3 |
| Ectodermal-neural cortex (with BTB-like domain) | 3.8 | 1.4 | 4.3 | 1.1 |
| Hepatic dihydrodiol dehydrogenase | 3 | 2.6 | 4.6 | 2.5 |
| Profilin 2 | 4.2 | 4.4 | 2.6 | 4.2 |
| Tumor rejection antigen (gp96) | 3 | 2.29 | 0.29 | 1.33 |
| X-ray repair complementing defective repairin | 3 | 3.3 | 4.3 | 0 |
| Estrogen Like Receptor NR3C2 | 4.2 | 4.5 | 2.5 | 1.33 |
| Casein kinase 2, beta polypeptide | 3 | 1.34 | 1.44 | 2.75 |
| Interleukin 13 receptor, alpha 2 (IL 13ra2) | 5.1 | 4.3 | 1.88 | 4.3 |
| Interleukin 7 receptor (IL 7r) | 14.8 | 5.7 | 5.7 | 5.7 |
| Chemokine (C-X-C motif) ligand 12 | 11.4 | 6.4 | 8 | 9.2 |
| Transforming growth factor, beta receptor 1 (TGFbR1) | 9.3 | 5.6 | 8.5 | 4.56 |
| | 6.2 | 2.1 | 3.5 | 3.6 |
| Chemokine (C-C motif) receptor 5 (CCR5) | 6.4 | 5.1 | 2.1 | 1.6 |
| Interleukin 2 receptor, alpha chain (IL2ra) | 5 | 3.4 | 4.6 | 2.7 |
| Chemokine (C-X-C motif) ligand 15 (CXCL | 4.5 | 3.3 | 5.6 | 1.3 |

FIGURE 3E

| | | | | |
|---|---|---|---|---|
| 15) | | | | |
| Colony-stimulating factor 2 receptor, alpha, lowaffinity (granulocyte-macrophage) (CSF2ra) | 4 | 2.05 | 1.1 | 2.3 |
| Chemokine (C motif) XC receptor 1 (XCR1) | | | | |
| Interleukin 11 receptor, alpha chain 1 (IL11ra) | 4.6 | 2.4 | 6.3 | 5.6 |
| Transforming growth factor, beta 2 (TGFb2) | 3.9 | 5.5 | 7.3 | 3.5 |
| Chemokine (C-C motif) receptor 7 (CCR7) | 3.4 | 2.3 | 3.3 | 1.11 |
| Interleukin 12 receptor, beta 2 (IL12rb2) | 3.1 | 2.9 | 3.2 | 4.8 |
| Chemokine (C-X-C motif) ligand 1 (CXCL1) | 3.4 | 8 | 7 | 1.2 |
| Chemokine (C-C motif) receptor 1-like 1 (CCR1l1) | 3.5 | 3.8 | 6.7 | 2.88 |
| Chemokine (C-C motif) ligand 11 (CCL11/eotaxin) | 3.2 | 0 | 1.2 | 2.2 |
| Chemokine (C-X-C motif) receptor 4 (CXCR4) | 4.7 | 2.1 | 2.9 | 1.64 |
| Low-density lipoprotein receptor | 3.53 | 3.44 | 1.75 | 1.73 |
| Adipose differentiation-related protein | 4.5 | 5.7 | 7.9 | 11.5 |
| Apolipoprotein C-III | 4.9 | 4.3 | 2.12 | 1.1 |
| Claudin 3 | 4.6 | 8.55 | 7.73 | 3.2 |
| Cellular retinoic acid binding protein 2 | 3.6 | 0 | 3.3 | 1.66 |
| Sequestosome 1 | 4.1 | 1.3 | 2.2 | 3.1 |
| Liver X receptor like NR1H2 | 3.8 | 4.7 | 1.5 | 7.3 |
| Aldehyde dehydrogenase 1 | 4.2 | 3.3 | 6.42 | 8.9 |

FIGURE 3F

| | | | | |
|---|---|---|---|---|
| family, member A1 | | | | |
| Heat shock 10 kda protein 1 (chaperonin 10) | 3.7 | 6.5 | 4.22 | 1.18 |
| Cyclin D1 (PRAD1: parathyroid adenomatosis 1) | 3.2 | 1.43 | 3.3 | 3.7 |
| Chromosome 7 open reading frame 24 | 4.1 | 1.2 | 2.65 | 4.4 |
| Aldehyde dehydrogenase 3 family, member B1 | 3 | 5.6 | 9.86 | 5.6 |
| Phosphatidylserine synthase 1 | 3 | 4 | 2.5 | 6.3 |
| Activin A receptor, type IB | 4.4 | 6 | 8.55 | 3.91 |
| Chemokine (C-C motif) ligand 25 (CCL 25) | 3.8 | 3.5 | 0 | 3.11 |
| Tumor necrosis factor (TNF) | 5.7 | 2.3 | 5.5 | 2.3 |
| Interleukin 21 receptor (IL 21r) | 3.5 | 8.9 | 5.5 | 6 |
| Chemokine (C-C motif) receptor-like 2 (CCRl2) | 6 | 6 | 2.22 | 1.28 |
| Interleukin 10 receptor, beta (IL 10rb) | 7 | 2.64 | 3.55 | 4.4 |
| Interleukin 15 receptor, alpha chain (IL 15ra) | 3.7 | 4.5 | 5.5 | 5.5 |
| Interleukin 13 (IL 13) | 4.5 | 8.3 | 4.6 | 9.4 |
| Interleukin 1 receptor, type II (IL 1r2) | 6 | 2.7 | 1.7 | 4.9 |
| Interleukin 2 receptor, gamma chain (IL 2rg) | 4 | 2.1 | 0 | 2.1 |
| Interleukin 1 receptor antagonist (IL 1rn) | 3.1 | 4.5 | 0 | 1.82 |
| Interleukin 6 signal transducer (IL 6st) | 3.1 | 9.5 | 0 | 9.5 |
| Interleukin 9 receptor (IL 9r) | 3.4 | 7.4 | 2.3 | 0.55 |
| Transforming growth factor, beta receptor | 4.1 | 2.7 | 4.9 | 3.44 |

FIGURE 3G

| | | | | |
|---|---|---|---|---|
| III (TGFbr 3) | | | | |
| Interleukin 5 receptor, alpha (IL 5ra) | 3.3 | 4.1 | 5.9 | 7 |
| Colony-stimulating factor 3 receptor (granulocyte) (CSF3r) | 0 | 0 | 1.33 | 0 |
| Lymphotoxin A (LTA) | 3.9 | 0 | 1.5 | 0 |
| Colony-stimulating factor 2 receptor, beta 2, | 3.2 | 0 | 5.5 | 5.5 |
| low-affinity (granulocyte-macrophage) (CSF2rb2) | 3.2 | 4.4 | 4.8 | 4.4 |
| Chemokine (C-C motif) ligand 7 (CCL7) | 1.9 | 3.4 | 0 | 3.05 |
| Colony stimulating factor 2 (granulocytemacrophage) (CSF2) | | | | |
| Chemokine (C-X-C motif) ligand 5 (CXCL 5) | 4.4 | 2.3 | 1.2 | 5.4 |
| Interleukin 1 receptor, type 1 (IL 1r1) | 13 | 6.1 | 5.7 | 3.3 |
| Chemokine (C-C motif) ligand 17 (CCL 17) | 3.11 | 4.09 | 1.13 | 4.3 |
| IL-13 receptor alpha chain (IL 13ra1) | 3.8 | 4.34 | 2.5 | 1.07 |
| Chemokine (C-C motif) ligand 1 (CCL 1) | 3.1 | 4.25 | 4.5 | 1 |
| Interleukin 18 receptor accessory protein (IL18rap) | 3.1 | 8.22 | 3.8 | 1.88 |
| Chemokine (C-C motif) ligand 9 (CCL 9) | 2.1 | 6.59 | 5.14 | 3.48 |
| Chemokine (C-C motif) ligand 12 (CCL 12) | 3 | 4.5 | 4.5 | 13.44 |
| Chemokine (C-C motif) ligand 8 (CCL 8) | 3 | 7.32 | 1.74 | 4.79 |

FIGURE 3H

| Interleukin 1 beta (IL 1b) | 3 | 2.5 | 7.47 | 6.16 |

FIGURE 7

| Class | Receptor | Subtype | Denomination | Ligand | Response Element | Monomer, Homodimer, or Heterodimer |
|---|---|---|---|---|---|---|
| Class I | TR | α, β | Thyroid hormone receptor | Thyroid hormone ($T_3$) | Pal, DR-4, IP | H |
| | RAR | α, β, γ | Retinoic acid receptor | Retinoic acid | DR-2, DR-5 | H |
| | VDR | | Vitamin D receptor | 1-25(OH)$_2$ vitamin D$_3$ | Pal, IP DR-3, IP-9 | H |
| | PPAR | α, β, γ | Peroxisome proliferator activated receptor | Benzotriene B4; Wy 14,643 Eicosanoids; thiazolidinediones (TZDs); 15-deoxy-12,41-prostaglandin J$_2$; polyunsaturated fatty acids | DR-1 | H |
| | PXR | | Pregnane X receptor | Pregnanes; C21 steroids | DR-3 | H |
| | CAR/MB67 | α, β | Constitutive androstane receptor | Androstanes; 1,4-bis[2-(3,5-dichloropyridyloxy)]benzene | DR-5 | H |
| | LXR | α, β | Liver X receptor | Oxysterols | DR-4 | H |
| | FXR | | Farnesoid X receptor | Bile acids | DR-4, IR-1 | H |
| | RevErb | α, β | Reverse ErbA | Unknown | DR-2, Hemisite | M, D |
| | RZR/ROR | α, β, γ | Retinoid Z receptor/retinoic acid-related orphan receptor | Unknown | Hemisite | M |
| | UR | | Ubiquitous receptor | Unknown | DR-4 | H |
| Class II | RXR | α, β, γ | Retinoid X receptor | 9-Cis-retinoic acid | Pal, DR-1 | D |
| | COUP-TF | α, β, γ | Chicken ovalbumin upstream promoter transcription factor | Unknown | Pal, DR-5 | D, H |
| | HNF-4 | α, β, γ | Hepatocyte nuclear factor 4 | Fatty acyl-CoA thioesters | DR-1, DR-2 | D |
| | TLX | | Tailless-related receptor | Unknown | DR-1, Hemisite | M, D |
| | PNR | | Photoreceptor-specific nuclear receptor | Unknown | DR-1, Hemisite | M, D |
| | TR2 | | Testis receptor | Unknown | DR-1 to DR5 | D, H |
| Class III | GR | | Glucocorticoid receptor | Glucocorticoids | Pal | D |
| | AR | | Androgen receptor | Androgens | Pal | D |
| | PR | | Progesterone receptor | Progestins | Pal | D |
| | ER | α, β | Estrogen Receptor | Estradiol | Pal | D |
| | ERR | α, β, γ | Estrogen-related receptor | Unknown | Pal, Hemisite | M, D |
| Class IV | NGFI-B | α, β, γ | NGF-induced clone B | Unknown | Pal, DR-5 | M, D, H |
| Class V | SF-1/FTZ-F1 | α, β | Steroidogenic factor 1 Fushi Tarazu factor 1 | Oxysterols | Hemisite | M |
| Class VI | GCNF | | Germ cell nuclear factor | Unknown | DR-0 | D |
| Class 0 | SHP | | Small heterodimeric partner | Unknown | | H |
| | DAX-1 | | Dosage-sensitive sex reversal | Unknown | | |

M, monomer; D, homodimer; H, heterodimer; NGF, nerve growth factor; DR, direct repeat; Pal, palindrome; IP, inverted palindrome

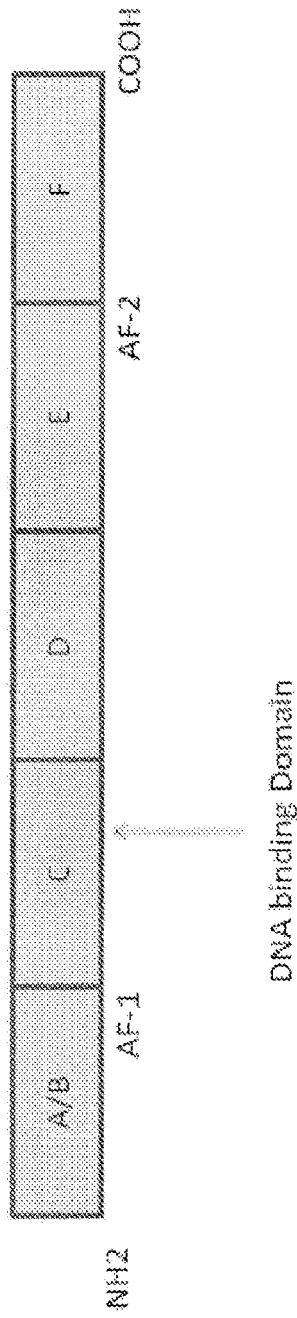

FIGURE 9A

| Name | Source [33] | Target receptors [33][34] | Target cells [33] | Function [33] |
|---|---|---|---|---|
| IL-1 | macrophages, B cells, monocytes,[35] dendritic cells [35] | CD121a/IL1R1, CD121b/IL1R2 | T helper cells | co-stimulation [35] |
| | | | B cells | maturation & proliferation [35] |
| | | | NK cells | activation[35] |
| | | | macrophages, endothelium, other | inflammation,[35] small amounts induce acute phase reaction, large amounts induce fever |
| IL-2 | Th1-cells | CD25/IL2RA, CD122/IL2RB, CD132/IL2RG | activated[35] T cells and B cells, NK cells, macrophages, oligodendrocytes | stimulates growth and differentiation of T cell response. Can be used in immunotherapy to treat cancer or suppressed for transplant patients. Has also been used in clinical trials (ESPIRIT, Stalwart) to raise CD4 counts in HIV positive patients. |
| IL-3 | activated T helper cells,[35] mast cells, NK cells, endothelium, eosinophils | CD123/IL3RA, CD131/IL3RB | hematopoietic stem cells | differentiation and proliferation of myeloid progenitor cells [35] to e.g. erythrocytes, granulocytes |
| | | | mast cells | growth and histamine release[35] |
| IL-4 | Th2 cells, just activated naive CD4+ cell, memory CD4+ cells, mast cells, macrophages | CD124/IL4R, CD132/IL2RG | activated B cells | proliferation and differentiation, IgG1 and IgE synthesis.[35] Important role in allergic response (IgE) |
| | | | T cells | proliferation[35] |
| | | | endothelium | |
| IL-5 | Th2 cells, mast cells, eosinophils | CD125/IL5RA, CD131/IL3RB | eosinophils | production |
| | | | B cells | differentiation, IgA production |
| IL-6 | macrophages, Th2 cells, B cells, astrocytes, endothelium | CD126/IL6RA, CD130/IR6RB | activated B cells | differentiation into plasma cells |
| | | | plasma cells | antibody secretion |
| | | | hematopoietic stem cells | differentiation |
| | | | T cells, others | induces acute phase reaction, hematopoiesis, differentiation, inflammation |
| IL-7 | Bone marrow stromal cells and thymus stromal cells | CD127/IL7RA, CD132/IL2RG | pre/pro-B cell, pre/pro-T cell, NK cells | differentiation and proliferation of lymphoid progenitor cells, involved in B, T, and NK cell survival, development, and homeostasis, ↑proinflammatorycytokines |
| IL-8 or CXCL8 | macrophages, lymphocytes, epithelial cells, endothelial cells | CXCR1/IL8RA, CXCR2/IL8RB/CD128 | neutrophils, basophils, lymphocytes | Neutrophil chemotaxis |
| IL-9 | Th2 cells, specifically by CD4+ helper cells | CD129/IL9R | T cells, B cells | Potentiates IgM, IgG, IgE, stimulates mast cells |
| IL-10 | monocytes, Th2 cells, CD8+ T cells, mast cells, macrophages, B cell subset | CD210/IL10RA, CDW210B/IL10RB | macrophages | cytokine production[35] |
| | | | B cells | activation [35] |
| | | | mast cells | |
| | | | Th1 cells | inhibits Th1 cytokine production (IFN-γ, TNF-β, IL-2) |
| | | | Th2 cells | Stimulation |
| IL-11 | bone marrow stroma | IL11RA | bone marrow stroma | acute phase protein production, osteoclast formation |
| IL-12 | dendritic cells, B cells, T | CD212/IL12RB1, IR12RB2 | activated [35] T cells, | differentiation into Cytotoxic T cells with IL-2,[35] ↑ IFN-γ, TNF-α, ↓ IL-10 |

FIGURE 9B

| | | | | |
|---|---|---|---|---|
| | cells, macrophages | | NK cells | ↑ IFN-γ, TNF-α |
| IL-13 | activated Th2 cells, mast cells, NK cells | IL13R | TH2-cells, B cells, macrophages | Stimulates growth and differentiation of B cells (IgE), inhibits TH1-cells and the production of macrophage inflammatory cytokines (e.g. IL-1, IL-6), ↓ IL-8, IL-10, IL-12 |
| IL-14 | T cells and certain malignant B cells | | activated B cells | controls the growth and proliferation of B cells, inhibits Ig secretion |
| IL-15 | mononuclear phagocytes (and some other cells), especially macrophages following infection by virus(es) | IL15RA | T cells, activated B cells | Induces production of Natural killer cells |
| IL-16 | lymphocytes, epithelial cells, eosinophils, CD8+ T cells | CD4 | CD4+ T cells (Th-cells) | CD4+ chemoattractant |
| IL-17 | T helper 17 cells (Th17) | CDw217/IL17RA, IL17 RB | epithelium, endothelium, other | osteoclastogenesis, angiogenesis, ↑ inflammatory cytokines |
| IL-18 | macrophages | CDw218a/IL18R1 | Th1 cells, NK cells | Induces production of IFNγ, ↑ NK cell activity |
| IL-19 | - | IL20R | | - |
| IL-20 | - | IL20R | | regulates proliferation and differentiation of keratinocytes |
| IL-21 | activated T helper cells, NKT cells | IL21R | All lymphocytes, dendritic cells | costimulates activation and proliferation of CD8+ T cells, augment NK cytotoxicity, augments CD40-driven B cell proliferation, differentiation and isotype switching, promotes differentiation of Th17 cells |
| IL-22 | - | IL22R | | Activates STAT1 and STAT3 and increases production of acute phase proteins such as serum amyloid A, Alpha 1-antichymotrypsin and haptoglobin in hepatoma cell lines |
| IL-23 | - | IL23R | | Increases angiogenesis but reduces CD8 T-cell infiltration |
| IL-24 | - | IL20R | | Plays important roles in tumor suppression, wound healing and psoriasis by influencing cell survival. |
| IL-25 | - | LY6E | | Induces the production IL-4, IL-5 and IL-13, which stimulate eosinophil expansion |
| IL-26 | - | IL20R1 | | Enhances secretion of IL-10 and IL-8 and cell surface expression of CD54 on epithelial cells |
| IL-27 | - | IL27RA | | Regulates the activity of B lymphocyte and T lymphocytes |
| IL-28 | - | IL28R | | Plays a role in immune defense against viruses |
| IL-29 | - | | | Plays a role in host defenses against microbes |
| IL-30 | - | | | Forms one chain of IL-27 |
| IL-31 | - | IL31RA | | May play a role in inflammation of the skin |
| IL-32 | - | | | Induces monocytes and macrophages to secrete TNF-α, IL-8 and CXCL2 |
| IL-33 | - | | | Induces helper T cells to produce type 2 cytokine |
| IL-35 | regulatory T cells | | | Suppression of T helper cell activation |

A

D

E

G

J

K

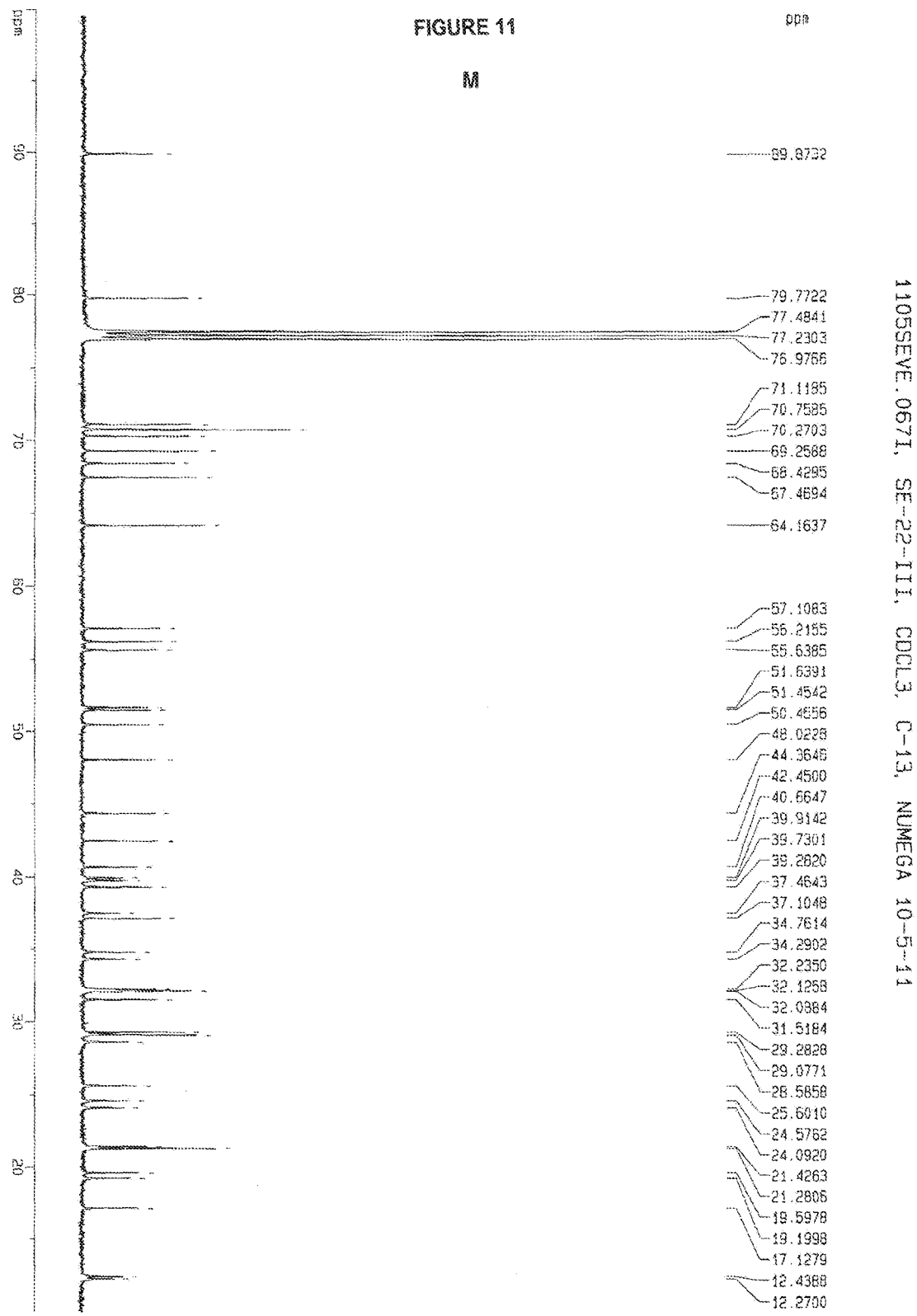

PLANT STEROIDS AND USES THEREOF

FIELD OF THE INVENTION

The present invention relates to plant steroids, including plant sterols, and more particularly, using plant steroids as drug delivery vehicles.

BACKGROUND OF THE INVENTION

Negative side effects can be associated with systemic exposure to oral drugs that are absorbed into the blood stream through the intestine, and circulate throughout the body. For some drugs, in particular those that are indicated for gastrointestinal symptoms or for those that exert their effects through the gastrointestinal system, it is desirable to keep the drugs within gastrointestinal tissues, such as intestinal cells, rather than circulating through the body. Accordingly, there is a need in the art for methods of specifically targeting drugs to intestinal cells.

SUMMARY OF THE INVENTION

Provided herein is a compound comprising a plant steroid and a drug. The plant steroid may be attached to the drug, and the attachment may be a conjugated bond or an amine bond. The drug may be an anti-inflammatory drug, a glucocorticoid, a LXR agonist, a TNFα inhibitor, a NF-κB inhibitor or agonist, a selective COX-2 inhibitor, a non-selective non-steroidal anti-inflammatory drug (NSAID), methotrexate, leflunomide, mesalamine, balsalaside, osalazine, sulfasalazine, an aminosalicylate, cyclosporine, mercaptopurine, azathioprine, atropine, a microsomal triglyceride transfer protein (MTP) inhibitor, an acyl CoA:cholesterol acyltransferase-2 (ACAT 2) inhibitor, a farnesoid X receptor (FXR) agonist, a diacylglycerol actyltransferase (DGAT) inhibitor, a glucagon-like peptide-1 (GLP-1) agonist, an ileal bile acid transport (IBAT) inhibitor, an antibiotic, or an antiviral. The drug may also be prednisone.

The plant steroid may be phytosterol or phytostanol. The sterol may be stigmasterol, brassicasterol, campesterol, or campesterol. Cholesterol may also be attached to the drug. Also provided herein is a method for lowering cholesterol levels, which may comprise administering an oxyphytostanol to a mammal in need thereof.

Also provided herein is a drug conjugate of formula (I),

D-L-P    (I), in which D is a drug constituent, L is a linkage, and P is a plant steroid constituent. Cholesterol may be substituted for the plant steroid constituent. D may be a drug as described above. For example, D may be a glucocorticoid or a LXR agonist constituent. The glucocorticoid may be budesonide, and the LXR agonist may be GW-3965 or TO-901317. P may be a phytosterol or phytostanol constituent. P may be stigmasterol, campesterol, 24(S),25-epoxycholesterol, or 5-6-epoxycampesterol. L may be a bond, and may comprise at least one chemical functional group, such as ether, amide, sulfonamide, or ester. L may comprise at least 3 atoms, and may comprise at least 10 atoms.

The drug conjugate may be a campesterol/budesonide drug conjugate, a 24(S),25-epoxycholesterol/budesonide drug conjugate, a campesterol/GW-3965 drug conjugate, a campesterol/TO-901317 drug conjugate, a 24(S),25-epoxycholesterol/GW-3965 drug conjugate, or a 24(S),25-epoxycholesterol/TO-901317 drug conjugate. The drug conjugate may be prednisolone stigmasteroltrisethyleneglycolalcohol succinate, prednisolone stigmasterol succinate, or prednisolone stigmasteroltrisethyleneglycol acetate.

BRIEF DESCRIPTION OF THE DRAWINGS

FIGS. 3A-H show gene expression changes in Caco-2 cells treated with various sterol-conjugated prednisone compounds.

FIG. 7 shows a list of classical and orphan hormone receptors and their ligands.

FIG. 8 shows a schematic of a nuclear hormone receptor. A typical nuclear receptor is composed of several functional domains. The variable NH2-terminal region (A/B) contains the ligand-independent AF-1 transactivation domain. The conserved DNA-binding domain (DBD), or region C, is responsible for the recognition of specific DNA sequences. A variable linker region D connects the DBD to the conserved E/F region that contains the ligand-binding domain (LBD) as well as the dimerization surface. The ligand-independent transcriptional activation domain is contained within the A/B region, and the ligand-dependent AF-2 core transactivation domain within the COOH-terminal portion of the LBD.

FIGS. 9A and B show a reference list of interleukin-related genes affected by prednisolone, SE-22, SE-24 and SE-41.

DETAILED DESCRIPTION

Figure 1:
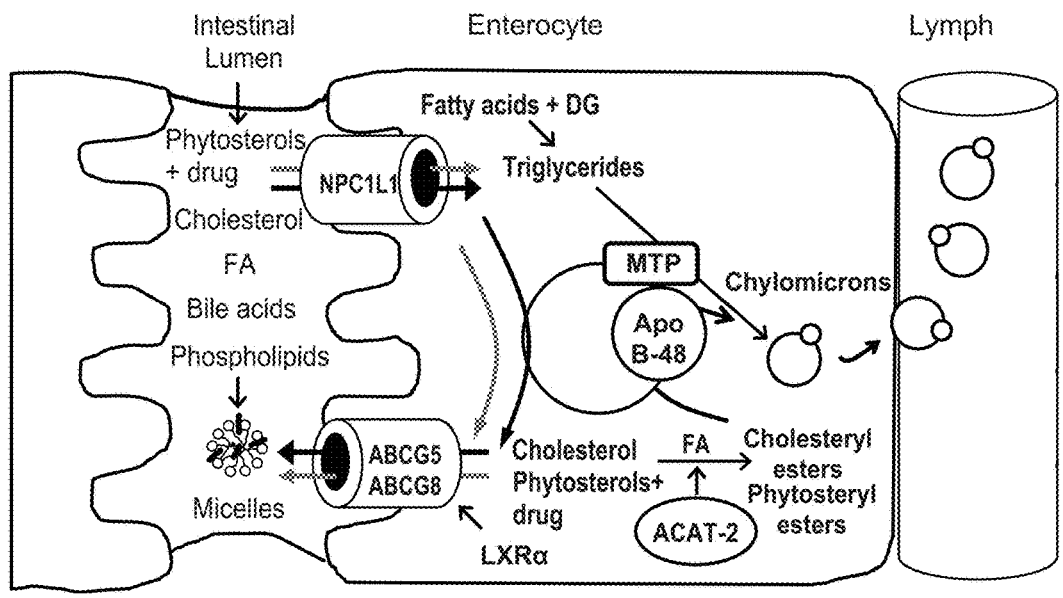
FIG. 1 shows how phytosterols and phytostanols are used to deliver drugs to intestinal cells.

The inventors have made the surprising discovery that plant steroid drug conjugates can be used to target intestinal cells for treatment of diseases of the intestine or to affect intestinal metabolism, without the adverse effects of systemic drug circulation. Specifically, attaching drugs to plant steroids by bonds that are temporarily or permanently (somewhat or entirely) resistant to digestion can result in targeted delivery of therapies to the intestinal cells without significant systemic absorption into the bloodstream.

1. Definitions

Unless otherwise defined, all technical and scientific terms used herein have the same meaning as commonly understood by one of ordinary skill in the art to which this invention pertains. In case of conflict, the present document, including definitions, will control.

The terminology used herein is for the purpose of describing particular embodiments only and is not intended to be limiting. The terms "a," "an" and "the" include singular and plural referents unless the context clearly dictates otherwise. Thus, for example, references to a composition for delivering "a drug" include reference to one, two or more drugs. The terms "comprise(s)," "include(s)," "having," "has," "can," "contain(s)," and variants thereof, as used herein, are intended to be open-ended transitional phrases, terms, or words that do not preclude the possibility of additional acts, compounds or structures. The present invention also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The terms "drug," "drug moiety," "drug constituent," "therapeutic," "therapeutic agent," and variants thereof, as used herein, refer to any drug or other agent that is intended for delivery to a targeted cell or tissue.

The term "linkage," "linker," and variants thereof, as used herein, refers to any moiety that connects the plant steroid constituent and the drug constituent. The linkage can be a covalent bond or a chemical functional group that directly connects the drug and the plant steroid. The linkage can contain a series of covalently bonded atoms and their substituents which are collectively referred to as a linkage. In certain embodiments, linkages can be characterized by a first covalent bond or a chemical functional group that connects the drug to a first end of the linker and a second covalent bond or chemical functional group that connects the second end of the linker to the plant steroid.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Compounds of the Invention

Provided herein are compounds for targeted drug delivery. In particular, provided herein are agents or drug conjugates comprising a plant steroid and a drug. Drug conjugates of the present invention comprise compounds of Formula (I)

D-L-P    (I)

wherein
D is a drug constituent;
L is a linkage; and
P is a plant steroid constituent.

In certain embodiments, the plant steroid (P) can be a phytosterol or a phytostanol. Phytosterols, and their saturated forms termed phytostanols, are a group of steroid alcohols that occur naturally in plants. These compounds cannot be synthesized by humans and therefore always originate in the diet. Phytosterols are poorly absorbed in the intestines (0.4-3.5%) while phytostanol absorption is even lower (0.02-0.3%). These plant based compounds are abundant in the diet, and enter the intestinal cells by the sterol transporter NPC 1L1. Once in the intestinal cells, plant sterols and stanols regulate nuclear receptors such as LXR and have other potential metabolic effects. Unlike intestinal cholesterol, however, these plant sterols and stanols are poor substrates for ACAT (an enzyme that is required to convert the sterol into an oleate for absorption into the lymph), and are actively transported out of the intestinal cells and back into the lumen by ABCG5 and ABCG8. For this reason, phytosterols and stanols typically are poorly absorbed into the bloodstream. Accordingly, phytosterols and stanols are suitable for use in targeted delivery of therapeutics to intestinal cells without systematic introduction into circulation.

In some embodiments, the resulting steroid-linker-drug conjugates are gradually or partially metabolized to one or more of its constituents (either steroid, linker, drug, steroid-linker, or linker-drug constituents or metabolic derivatives thereof). In certain embodiments, conjugates of this kind are useful as a delivery vehicle of the active moiety in the conjugate, beyond the early GI digestive stage. Once delivered down-stream, such conjugates may be metabolized to release the active moiety at the target site. Such conjugates may have pro-drug features. Although cholesterol may be used as a constituent in such partially stable conjugates, due to the risk of elevating cholesterol in the subject, phytosterols may be preferred as a constituent in such conjugates. In other embodiments, the resulting sterol-linker-drug conjugates are quite stable and metabolized to a limited extend in the body. For such relatively stable sterol-linker-drug conjugates there is limited preference of phytosterols over cholesterol.

Phytosterols suitable for use as the plant steroid constituent include, but are not limited to, β-sitosterol, campesterol, stigmasterol (stigmasta-5,22-dien-3β-ol), and brassicasterol (ergosta-5,22-dien-3β-ol). Phytostanols appropriate for use as the plant steroid constituent include, but are not limited to, sitostanol, campestanol, brassicastanol, and stigmastanol. In certain embodiments, the phytostanol may exist as an esterified form to provide a stanol ester. Alternatively, the plant steroid constituent may be a plant sterol that is oxidized, and thus may be an oxyphytosterol or an oxyphytostanol.

In another embodiment, the plant steroid (P) may be replaced with cholesterol. Cholesterol may be attached to the drug (D) in the same manner via the same linker (L) as described for plant sterols herein. Cholesterol may also be functionalized as described for plant sterols herein.

In a preferred embodiment, the plant steroid constituent of the drug conjugate is a compound of Formula (1a), also referred to as campesterol.

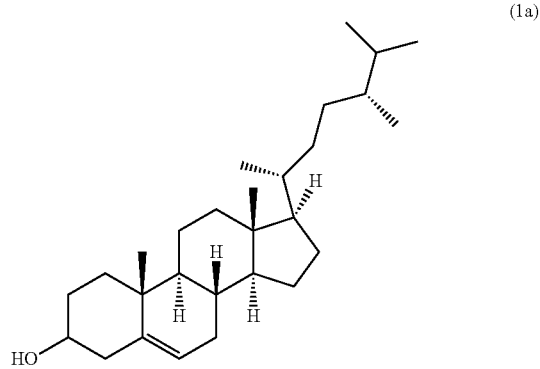

(1a)

In certain embodiments, amino, sulfur, and other derivatives of sterols may be used, including but not limited to, oxidized sterols such as 24(S),25-epoxycholesterol (Formula 1b) or 5-6-epoxycampesterol.

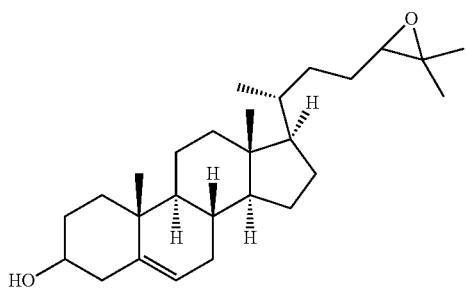
(1b)

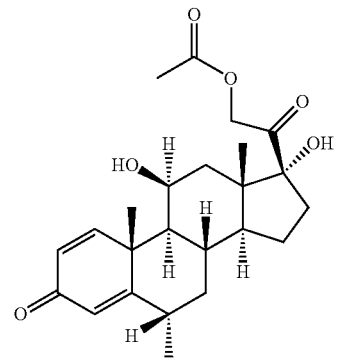
(1c)

In some embodiments of the present invention, the steroid may link directly to the drug. For instance, the —OH group on the steroid may react with a carboxy group on the drug to form an ester linkage. In other embodiments, a linker molecule may be used to provide a linkage between the steroid and drug constituents, tailored to optimize its drug delivery or metabolic stability characteristics as well as to optimize the synthesis of the desired type of molecule. In other embodiments the —OH group may be substituted with an amine, sulfur or other functionality.

Drugs suitable for use as the drug constituent (D) of the presently disclosed drug conjugates include any drug or therapeutic agent that is intended for delivery to a targeted cell or tissue. In certain embodiments, the therapeutic agent may be a drug for treating a disease of the intestine or that affects intestinal metabolism. For example, the drug may be used to treat inflammatory bowel disease or may be a chemotherapeutic agent for a cancer such as intestinal or colon cancer. In certain embodiments, the therapeutic agent is an anti-inflammatory, such as for example, a glucocorticoid, a LXR agonist, a TNFα inhibitor, an NF-κB inhibitor or agonist, a selective COX-2 inhibitor, or a non-selective non-steroidal anti-inflammatory drug (NSAID). The therapeutic agent may also be methotrexate, leflunomide, mesalamine, balsalaside, osalazine, sulfasalazine, an aminosalicylate, cyclosporine, mercaptopurine, azathioprine, atropine, a microsomal triglyceride transfer protein (MTP) inhibitor, an acyl CoA:cholesterol acyltransferase-2 (ACAT-2) inhibitor, a farnesoid X receptor (FXR) agonist, a diacylglycerol actyltransferase (DGAT) inhibitor, a glucagon-like peptide-1 (GLP-1) agonist, an ileal bile acid transport (IBAT) inhibitor, an antibiotic, or an antiviral.

Glucocorticoids include, without limitation, hydrocortisone, hydrocortisone acetate, cortisone acetate, tixocortol pivalate, prednisolone, methylprednisolone (Formula (1c)), prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

Liver X receptor agonists (LXR agonists) include, without limitation, GW-3965 (GlaxoSmithKline) depicted as Formula (1d), TO-901317 (Tularik) depicted as Formula (1e), MBX-102 (Metabolex), NO-1886 (Otsuka), and Gemcabene (Pfizer).

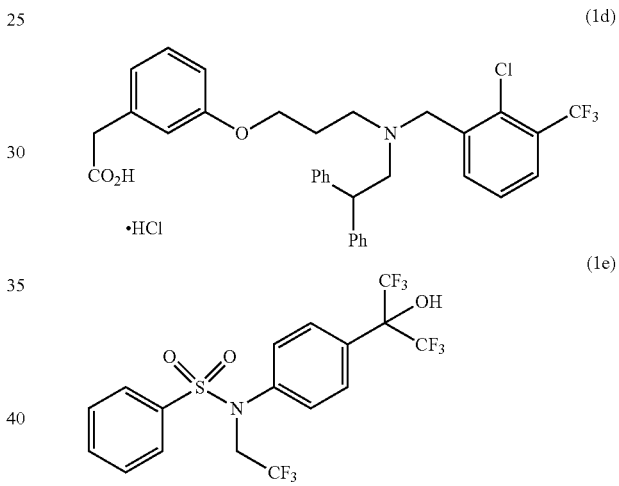
(1d)

(1e)

Selective cyclooxygenase-2 inhibitors (COX-2 inhibitors) include, without limitation, rofecoxib, brand name VIOXX™ (Merck & Co., Inc. Whitehouse Station, N.J., USA); celecoxib, brand name CELEBREX™ (Pfizer); valdecoxib, brand name BEXTRA™ (Pharmacia Corp., Peapack, N.J., USA); paracoxib, brand name DYNASTAT™ (Pharmacia Corp.); etoricoxib, brand name ARCOXIA™ (Merck & Co., Inc.); and NS-398 ((N-(2-cyclohexyloxy-4-nitrophenyl)methane sulphonamide).

NSAIDs contemplated for modification in accordance with the present invention include acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (iodine), fenoprofen calcium (nalfon), flurbiprofen (ansaid), indomethacin (indocin, indometh, others), ketoprofen (orudis, oruvail), carprofen, indoprofen, ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolnetin (tolectin), meloxicam, nabumetone, naproxen, lomoxicam, nimesulide, indoprofen, remifenzone, salsalate, tiaprofenic acid, flosulide, and the like. Presently preferred NSAIDs employed in the practice of the invention include naproxen, aspirin, ibuprofen, flurbiprofen, indomethacin, ketoprofen, carprofen, and the like.

MTP inhibitors include, without limitation, implitapide, BMS-201038, R-103757, JTT-130, and the like. ACAT-2 inhibitors include, without limitation, fatty acid anilide derivatives, urea-derived compounds, CI976, eflucimibe (F-11251), CP113,818, glibenclamide, avasimibe (CI-1011), pactimibe, rimonabant, AM251, SR144528, pyripyropene A, CP113, PD-138142-15, PD-156759, XD-793-11, AEGR-733, DuP128, and the like. FXR agonists include, without limitation, GW4064, INT-747, MFA-1, fexaramine, WAY-362450, T0901307, 6-ethylchenodeoxycholic acid, AGN29, AGN31, guggulsterone, and the like. DGAT inhibitors include, without limitation, T863, LCQ-908, PF-04620110, A-922500, H128, JTT-553, PF-4415060, xanthohumol, and the like. GLP-1 agonists include, without limitation, exenatide, liraglutide, taspaglutide, AVE-0010, albiglutide, R1583, and the like. IBAT inhibitors include, without limitation, A3309, SC-435, S-8921, 2164U90, BRL 39924A, and the like.

Preferably, the plant steroid constituent, such as a phytosterol or phytostanol, is linked to the therapeutic constituent through a bond or bonds resistant to digestion. In certain embodiments, the linkage (L) may be a bond, thereby directly linking the drug constituent (D) to the plant steroid constituent (P). Alternatively, the linkage between the plant steroid and the therapeutic includes one or more atoms. Preferably, the linkage includes ten or more atoms, particularly where relative proximity of the drug constituent to the sterol/stanol constituent may interfere with the intestinal cell's ability to recognize/attach to the sterol/stanol constituent for removal from the cell; and/or where relative proximity of the sterol/stanol constituent to the therapeutic may interfere with the therapeutic activity of the drug.

The linkage (L) between the plant steroid and the therapeutic may include one or more ether, amide, sulfonamide, and/or ester bonds. Ether bonds have a high degree of stability in biological systems, and thus may be preferred in certain embodiments. Amide and sulfonamide bonds resist typical digestion by esterases and proteases, but are often not resistant to liver metabolism. Accordingly, in certain embodiments, amide or sulfonamide linkages provide an extra safety measure compared to ether bonds, as a minor degree of absorption of the drug conjugate can be neutralized by liver metabolism, and thus avoid accumulation of in circulation. In certain embodiments, the linkage may include one or more ester bonds, which can be relatively stable to digestion. The linkage may comprise trisethylene glycol, succinic acid, multiple units thereof, or a combination of the foregoing.

The plant steroid may be conjugated to the drug using a functional linkage as follows.

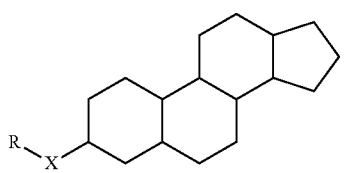

where X is O, S, N, NH, SO, SO$_2$, SONH, or the like; and R is H, or substituted alkyl or aralkyl with at least one functionality suitable for drug conjugation. The steroid nucleus structure above may be replaced by any plant steroid structure described herein.

In certain embodiments, the phytosterol or phytostanol can be linked to a drug constituent through a typical phytosterol or phytostanol hydroxyl group. Attachment to the plant steroid hydroxyl group can be accomplished without sacrificing the lack-of-absorbance feature of the plant steroids. For example, fatty acid esters of phytosterols and phytostanols have previously been used as agents to reduce LDL-cholesterol levels. Despite the chemical modification of the phytosterol or phytostanol hydroxyl group into a fatty acid ester, the lack-of-absorbance feature of the plant steroids is retained. Accordingly, a typical phytosterol or phytosterol hydroxyl group may be targeted for chemical modification in the attachment of the plant steroid to a drug constituent.

In one embodiment, a plant steroid constituent may be attached to a glucocorticoid. The plant steroid may be linked to the glucocorticoid, for example, via a ketone or hydroxyl functional group of the glucocorticoid. However, when comparing a broad range of natural and synthetic glucocorticoids, the distal (left side) ketone (═O) and the central hydroxyl (—OH) groups are highly conserved across the range. For example, the glucocorticoid of formula (1f), corresponding to budesonide, comprises the distal (left side) ketone (designated "a") and a central hydroxyl group (designated "b"). While these groups provide excellent functionality for linking a specific glucocorticoid to another constituent, such a link may reduce or potentially eliminate anti-inflammatory activity. Therefore, in certain embodiments, the distal ketone and central hydroxyl groups are conserved and other functionalities in the glucocorticoid are targeted for attachment to the plant steroid.

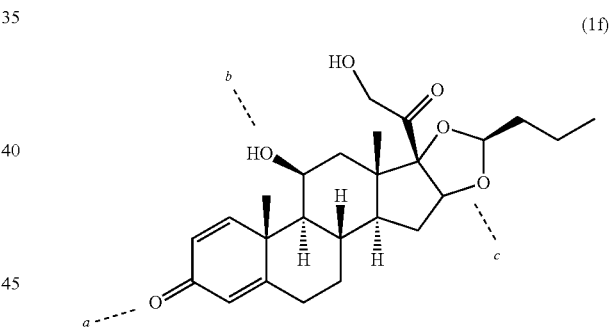

(1f)

A subgroup of synthetic glucocorticoids include a 1,3-dioxoalane ring fused to the typical glucocorticoid cyclopentane ring on the opposed distal side (right side) of the glucocorticoid molecule. The compound of formula (1f), budesonide, comprises a distal (right side) 1,3-dioxolane ring (designated "c"). This 1,3-dioxolane ring demonstrates substantial variation in attached substituent groups across the subgroup of synthetic glucocorticoids. Accordingly, in certain embodiments, these variable sites on the acetonide ring can be used for linking a glucocorticoid drug constituent to a plant steroid constituent.

For example, one exemplary drug conjugate of the present invention, depicted herein as formula (1g), comprises campesterol linked to the budesonide via the budesonide 1,3-dioxolane ring, wherein R is hydrogen, substituted or unsubstituted alkyl, or substituted or unsubstituted aralkyl. The campesterol/budesonide drug conjugate of formula (1g) includes a linkage (L) between the plant steroid and the glucocorticoid. The linkage includes an ester function (designated "e") at the campesterol and an amine function (designated "am") at the glucocorticoid.

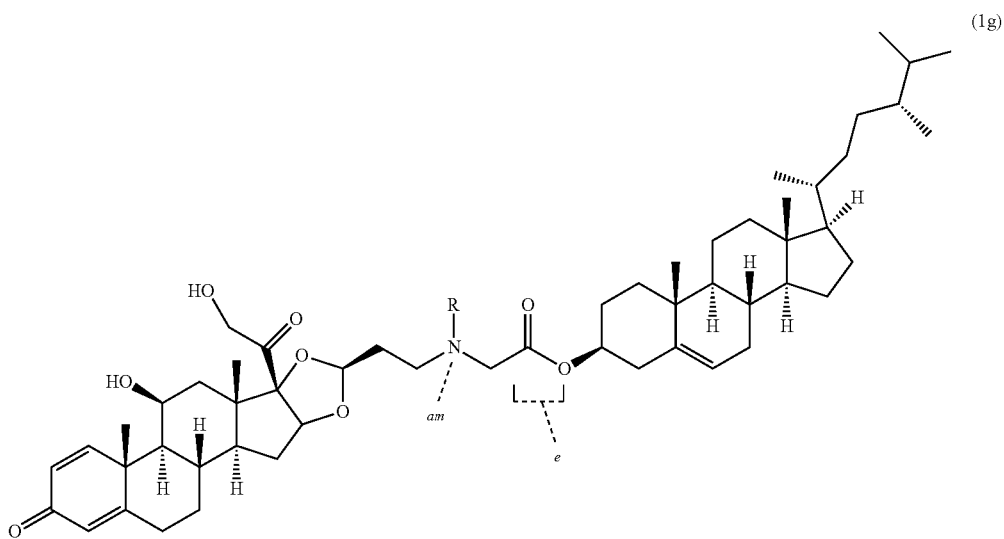

(1g)

Across the entire range of synthetic glucocorticoids substantial variation is found within sub-molecular groups attached to the north-side of the typical cyclopentane ring on the opposed distal side (right side) of the glucocorticoid molecule. These sub-molecular groups typically contain hydroxyl and ketone functionalities that are suitable for attaching the glucocorticoid to a plant steroid constituent. For example, one exemplary drug conjugate of the present invention, depicted herein as formula (1h), comprises budesonide and campesterol linked through an ether function at the campesterol and an ester function at the glucorticoid. The glucocorticoid is linked to the plant steroid via a sub-molecular group (an α-hydroxy ketone) that is attached to a fused ring carbon of the cyclopentane and 1,3-dioxolane rings of the glucocorticoid.

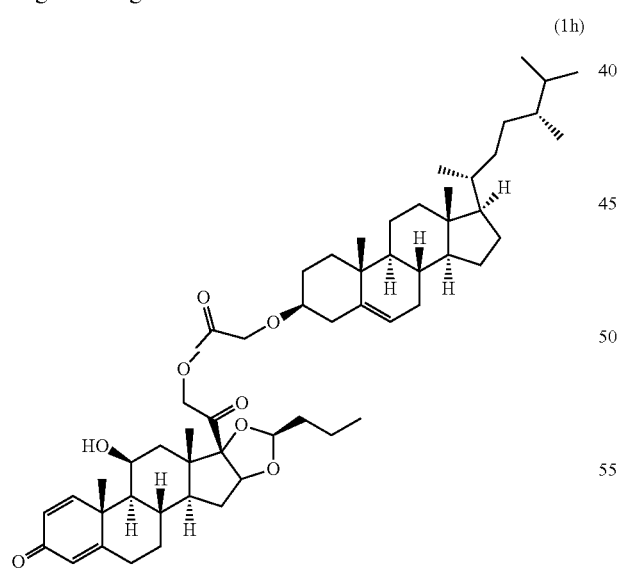

(1h)

In another example, an exemplary drug conjugate of the present invention, depicted herein as formula (1i) comprises budesonide linked to 24(S),25-epoxycholesterol through an ether function proximal the budesonide and an ester function at the plant steroid constituent. The glucocorticoid is linked to the plant steroid via a sub-molecular group (an α-hydroxy ketone) attached to a fused ring carbon of the cyclopentane and 1,3-dioxolane rings of the glucocorticoid.

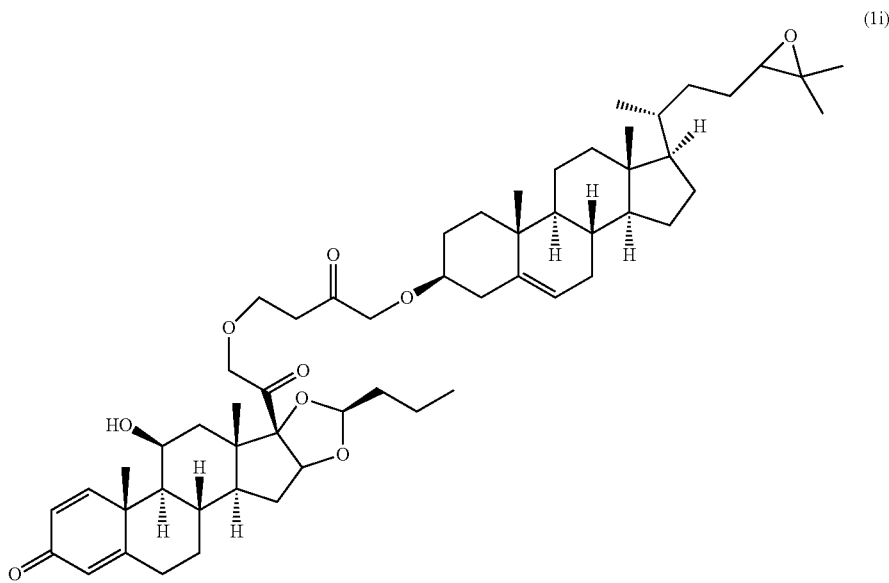

(1i)

In certain exemplary embodiments, a plant steroid constituent may be attached to a LXR agonist. LXR agonists, such as TO-901317 or GW-3965, comprise functional groups useful for creating a link to a plant steroid constituent. For example, GW-3965 includes a carboxy group function and TO-901317 includes a hydroxyl group function, both of which can be synthetically modified to link the LXR agonist to a plant steroid constituent.

One exemplary drug conjugate of the present invention, depicted herein as formula (1j), includes the LXR agonist GW-3965 linked to a phystosterol or phytostanol constituent (depicted generically), via the GW-3965 carboxy group and the left side hydroxyl group of the plant steroid. The linkage between the LXR agonist and plant steroid includes ester function at the LXR agonist and amine function at the plant steroid.

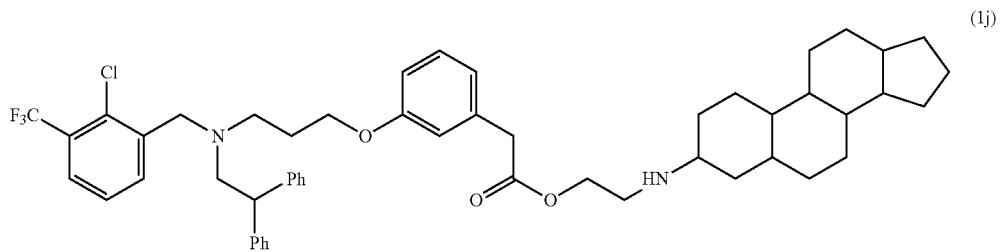 [SMILES: O=C(Cc1cccc(OCCCN(Cc2cccc(C(F)(F)F)c2Cl)CC(c2ccccc2)c2ccccc2)c1)OCCNC1CCC2C(CCC3C4CCCC4CCC23)C1]

(1j)

Another exemplary drug conjugate, depicted herein as formula (1k), includes GW-3965 linked to a phytosterol or phytostanol constituent via the GW-3965 carboxy group and the left side hydroxyl group of the plant steroid, wherein the linkage between the LXR agonist and plant steroid includes amide function at the LXR agonist and ether function at the plant steroid.

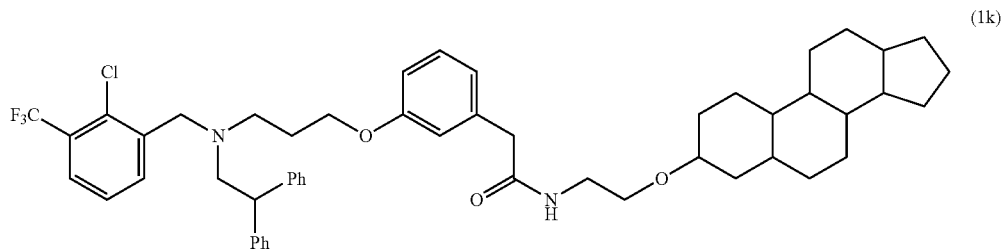 [SMILES: O=C(Cc1cccc(OCCCN(Cc2cccc(C(F)(F)F)c2Cl)CC(c2ccccc2)c2ccccc2)c1)NCCOC1CCC2C(CCC3C4CCCC4CCC23)C1]

(1k)

Another exemplary drug conjugate, depicted herein as formula (1m), includes TO-901317 linked to a phytosterol or phytostanol constituent via the TO-901317 hydroxyl group and the left side hydroxyl group of the plant steroid, wherein the linkage between the LXR agonist and plant steroid includes ether function at the LXR agonist and amide function at the plant steroid.

and the left side hydroxyl group of the plant steroid, wherein the linkage between the LXR agonist and plant steroid includes ether function at the LXR agonist and amine function at the plant steroid.

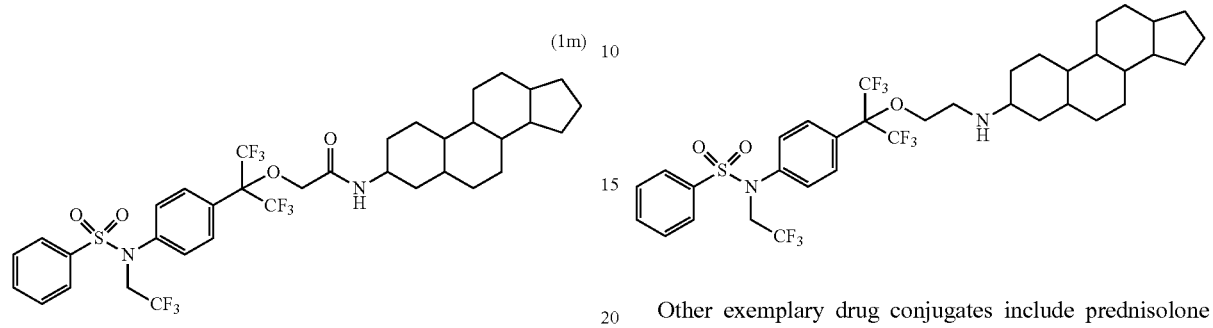

Another exemplary drug conjugate, depicted herein as formula (1n), includes TO-901317 linked to a phytosterol or phytostanol constituent via the TO-901317 hydroxyl group Other exemplary drug conjugates include prednisolone stigmasteroltrisethyleneglycolalcohol succinate (formula (1o)), prednisolone stigmasterol succinate (formula (1p)), and prednisolone stigmasteroltrisethyleneglycol acetate (formula (1q)).

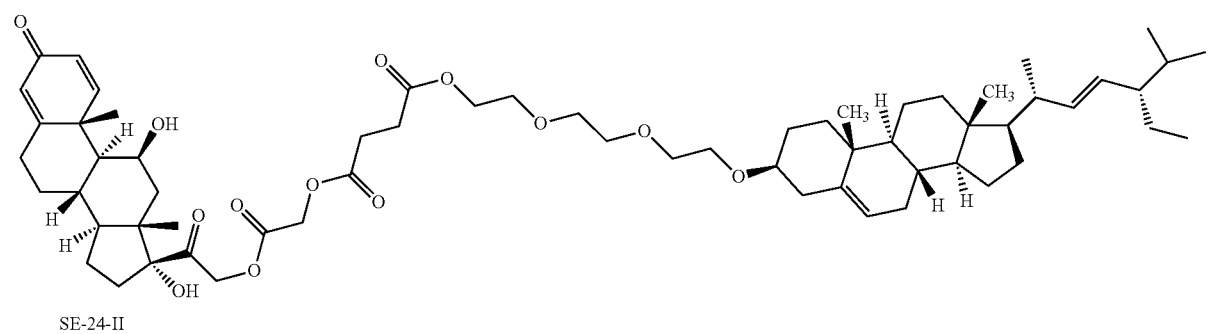

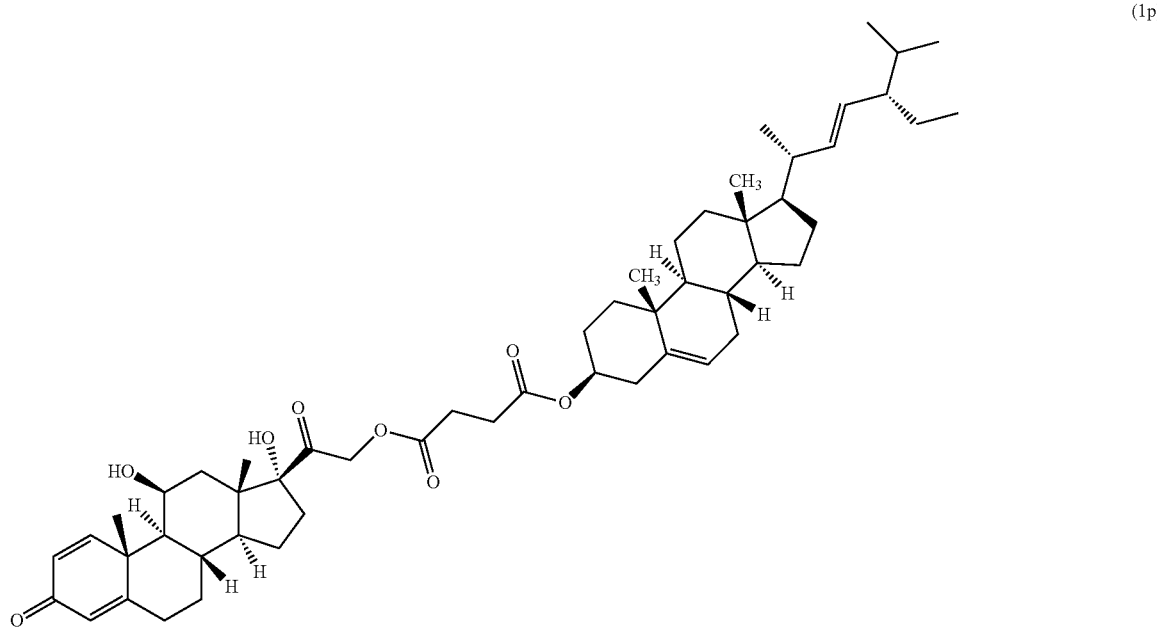

SE-41-II

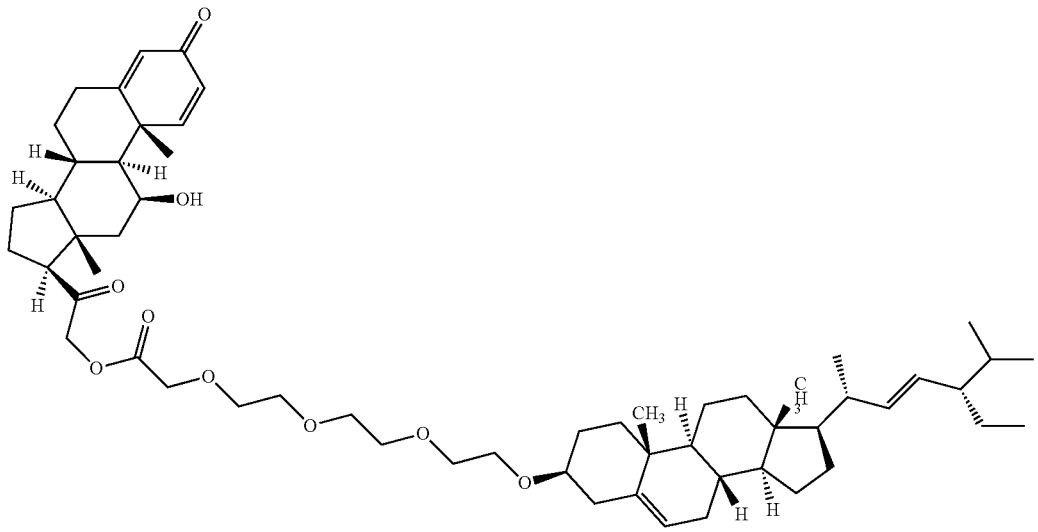

(1q)

3. Methods of Treatment

In another aspect, provided herein are methods of treating a disease by administering a drug conjugate in accordance with the present invention to a mammal in need thereof. The drug conjugate may be specifically delivered to intestinal cells as shown in FIG. 1.

Also provided herein is a method of modulating cholesterol levels such as LDL-C by administering the plant steroid. The modulated cholesterol may be serum or plasma. For example, an oxyphytostanol may be a potent ligand for LXR, which may result in greater LDL-C reduction than non-oxidized plant sterols and stanols, and significantly increase intestinally derived HDL metabolism. The drug conjugate may be used to treat cancer, such as intestinal or colon cancer, inflammatory bowel disease (IBD), celiac disease, irritable bowel syndrome, dyslipidemia, atherosclerosis, obesity, hypertriglyercidemia, diabetes, or intestinal infections.

The drug conjugate may also be used to treat gastro-intestinal diseases, including, without limitation, Crohn's disease, ulcerative colitis, inflammatory bowel disease, irritable bowel disease, irritable bowel syndrome (either diarrhea or constipation associated), celiac disease, gastro-intestinal inflammation associated with food-allergies or autistic spectrum disorder, gastritis (atrophic, Ménétrier's disease, gastroenteritis), emesis (nausea and vomiting), pyloric stenosis, achlorhydria, gastroparesis, portal hypertensive gastropathy, gastric antral vascular ectasia, gastric dumping syndrome, HMFs (Human Mullular Fibrilation syndrome), enteritis (duodenitis, jejunitis, ileitis), ulcers (peptic, duodenal, or Curling's ulcer), Dieulafoy's lesion, malabsorption (including but not limited to Coeliac, tropical sprue, Whipple's disease, steatorrhea, Milroy disease), colitis (pseudomembranous, ulcerative, ischemic, microscopic, collagenous, lymphocytic), megacolon/toxic megacolon, enterocolitis, necrotizing enterocolitis, functional colonic disease, intestinal pseudoobstruction, and Ogilvie syndrome.

The drug conjugate may also be used to treat inflammatory conditions, including, without limitation, arthritis, osteo-arthritis, asthma, COPD, allergies, seasonal allergies, food allergies, pruritis, urticaria, atopic allergy, and (atopic) dermatitis.

The drug conjugate may also be used to treat autoimmune diseases, including, without limitation, acute disseminated encephalomyelitis (ADEM), addison's disease, agammaglobulinemia, alopecia areata, amyotrophic lateral sclerosis (ALS), ankylosing spondylitis, antiphospholipid syndrome, antisynthetase syndrome, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease (Balo concentric sclerosis), Behçet's disease, Berger's disease, Bickerstaff's encephalitis, Blau syndrome, bullous pemphigoid, Castleman's disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, contact dermatitis, cranial arteritis, CREST syndrome, Cushing's Syndrome, cutaneous leukocytoclastic angiitis, Dego's disease, Dercum's disease, dermatitis herpetiformis, dermatomyositis, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura (autoimmune thrombocytopenic purpura), IgA nephropathy, inclusion body myositis, chronic inflammatory demyelinating polyneuropathy, interstitial cystitis, juvenile idiopathic arthritis (juvenile rheumatoid arthritis), Kawasaki's disease, Lambert-Eaton myasthenic syndrome, leukocytoclastic vasculitis, Lichen planus, Lichen sclerosus, linear IgA disease (LAD), Lou Gehrig's disease, lupoid hepatitis (autoimmune hepatitis), lupus erythematosus, Majeed syndrome, Ménière's disease, microscopic polyangiitis, Miller-Fisher syndrome (Guillain-Barre Syndrome), mixed connective tissue disease, morphea, Mucha-Habermann disease (pityriasis lichenoides et varioliformis acuta), multiple sclerosis, myasthenia gravis, myositis, narcolepsy, neuromyelitis optica (Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, pelapsing polychondritis, Reiter's syndrome, restless leg syndrome, retroperitoneal fibrosis, rheumatoid arthritis, rheumatic fever, sarcoidosis, Schmidt syndrome, Schnitzler syndrome, scleritis, scleroderma, serum Sickness, Sjögren's syndrome, spondyloarthropathy, Still's disease, stiff person syndrome, subacute bacterial endocarditis (SBE), Susac's syndrome, Sweet's syndrome, Sydenham chorea, sympathetic ophthalmia, systemic lupus erythematosis, Takayasu's arteritis, temporal arteritis, thrombocytopenia, Tolosa-Hunt syndrome, transverse myelitis, spondyloarthropathy, urticarial vasculitis, vasculitis, vitiligo, and Wegener's granulomatosis.

The drug conjugate may also be used to treat dyslipidemia and cardiovascular diseases, including, without limitation, hypercholesterolemia (primary and familial), hypertryglyceridemia (high and very high), mixed dyslipidemia, Fredrickson Type I, II, III, IV, and V dyslipidemia, atherosclerosis, coronary artery disease, coronary heart disease, cerebrovascular disease, peripheral artery disease.

The drug conjugate may also be used to treat diabetes and associated conditions, including, without limitation, insulin resistance, non insulin dependent diabetes mellitus (NIDDM), Type II diabetes, and Type 1 diabetes.

The drug conjugate may also be used to treat bacterial, viral, parasite or fungal infections, including, without limitation, gastro-intestinal infections, skin infections, eye-infections, respiratory system infections, ear infections, sexually transmitted diseases, airborne diseases, insect-transmitted diseases, transfusion or transplant transmitted diseases, and mother-to-child transmitted diseases.

The drug conjugate may also be used to treat cancers, including, without limitation, colon cancer, gastric cancer, pancreatic cancer, skin cancer, liver cancer, myeloma, melanoma, sarcoma, oral cancer, rectal cancer, mesothelioma, lymphoma, and other cancers.

The present invention has multiple aspects, illustrated by the following non-limiting examples.

Example 1

Methods of Making Plant Steroid-Conjugated Compounds

Stigmasterol Mesylate (SE-09-II)

A solution of stigmasterol (formula (1r)) (1.78 g) in 25 ml of methylene chloride was cooled to ~4° C. and 0.9 g of triethylamine added followed by the dropwise addition of 0.69 g of methanesulfonyl chloride in 3-4 ml of THF. The reaction mixture was stirred at 4° C. for 3 hr, the cooling bath removed and the reaction mixture stirred overnight at ambient temperature. The reaction was quenched with water and the phases separated. The organic phase was washed with 5% NaHCO$_3$, dried with Na$_2$SO4 and evaporated under reduced pressure to yield the desired product (stigmasterol mesylate; formula (1s)) used as is in the next step.

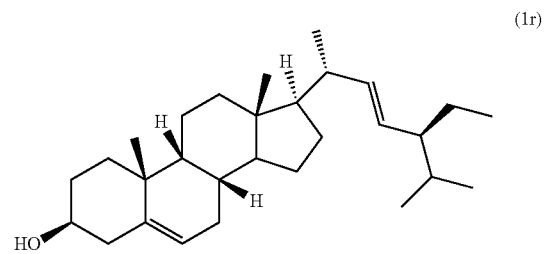

(1r)

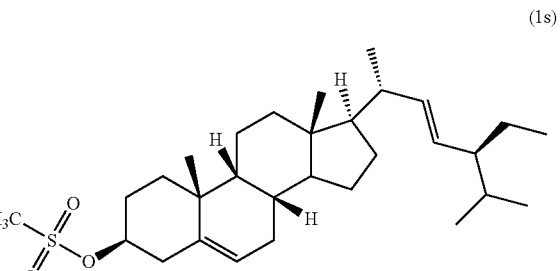

(1s)

Stigmasterol Triethyleneglycol Ether (SE-16-II)

Stigmasterol mesylate (3.0 g) and triethyleneglycol (21.0 g) were dissolved in ~15 ml of 1,4-dioxane and the reaction mixture heated at reflux, under nitrogen, for 3-4 hr. The reaction mixture was cooled to room temperature and the solvent removed under vacuum. The residue was partitioned between methylene chloride and water and the phases separated. The organic phase was washed sequentially with saturated NaHCO$_3$, water and brine, dried over Na$_2$SO$_4$ and the solvent removed under vacuum. The residue was purified by column chromatography (silica gel eluted with MTBE). The resulting product (stigmasterol triethyleneglycol ether; formula (1t)) was used in the next step.

SE-16-II

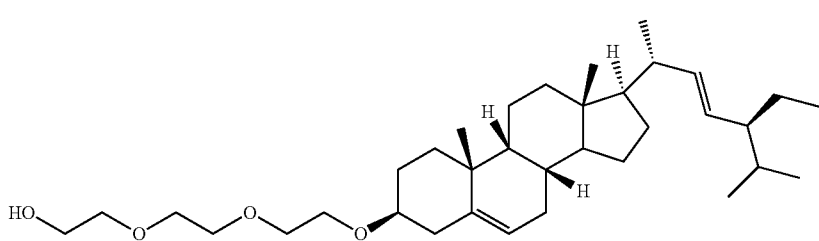

(1t)

Stigmasterol Triethyleneglycol Succinate Monoacid (SE-19-II)

Stigmasterol triethyleneglycol ether (0.55 g), succinic anhydride (0.12 g), triethylamine (0.20 g), and DMAP (20 mg) were dissolved in 15 ml of THF. The reaction mixture was stirred overnight at ambient temperature and ethyl acetate and water added. The phases were separated and the organic layer washed with 5% HCl followed by water. The organic layer was dried and the solvent removed under vacuum. The crude product (stigmaterol triethyleneglycol succinate; formula (1u)) was used as is.

SE-19-II

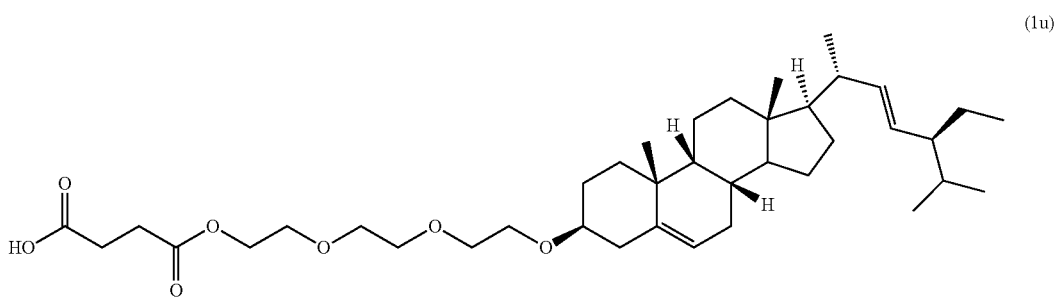

(1u)

Stigmasterol Triethyleneglycol Prednisolone Succinate (SE-22-II)

Stigmasterol triethylene glycol succinate monoacid (0.65 g) was dissolved in toluene (15 ml), cooled to 0° C. and oxalyl chloride (0.5 ml) added dropwise. The reaction mixture was stirred at ambient temperature for 1 hr, 60° C. for 1 hr, cooled to ambient temperature and evaporated to dryness under reduced pressure.

To a cooled (0-4° C.) solution of 0.36 g prednisolone in a mixture of THF and TEA was added the crude acid chloride prepared above. The reaction mixture was stirred overnight at ambient temperature and then refluxed for 1-3 hrs. The reaction mixture was cooled and ethyl acetate added. The organic phase was separated, washed with water, 1% NaHCO$_3$, dried over Na$_2$SO$_4$ and evaporated to dryness to yield the crude product. The crude product was purified by column chromatography on silica gel eluted with methylene chloride and then CH$_2$Cl$_2$/EtOAc 9:1. The resulting product was stigmasterol triethyleneglycol prednisone succinate (SE-22-II; formula (1o)).

Stigmasterol Triethyleneglycol Oxyacetic Acid (SE-39-II)

To stigmasterol triethyleneglycol (1 g) in THF was added sodium hydride (0.26 g, dry basis) as a 60 wt % suspension in mineral oil and 0.51 g bromoacetic acid and the reaction mixture stirred overnight at ambient temperature. After cooling to 0° C. the excess sodium hydride was destroyed by the slow addition of water. THF was evaporated under reduced pressure and the aqueous solution acidified with 6N HCl and extracted with methylene chloride. The methylene chloride extract was washed with water, dried with Na$_2$SO4 and evaporated to dryness under reduced pressure to give a waxy solid. This material (stigmasterol triethyleneglycol oxyacetic acid; formula (1v)) was used without further purification.

SE-39-II

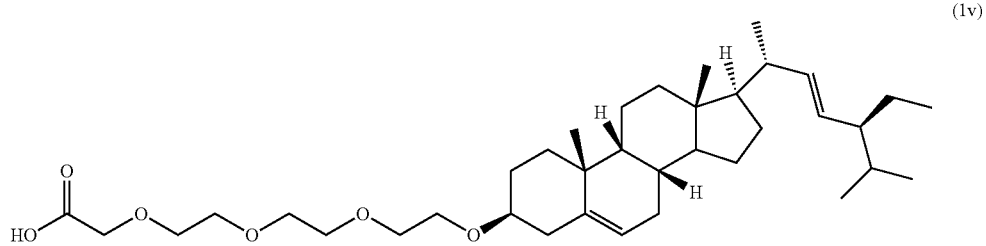

(1v)

Stigmasterol Triethyleneglycol Oxyacetic Acid Prednisolone Ester (SE-41-II)

See procedure for synthesis of stigmasterol triethyleneglycol prednisolone diester above. The crude product was purified by column chromatography on silica gel with $CH_2Cl_2/EtOAc$ 9:1, 8:2 as eluent and $CH_2Cl_2/MeOH$ 95:5.

Stigmasterol Succinate (SE-21-II)

A solution of stigmasterol (0.83 g), succinic anhydride (0.32 g), pyridine (1.5%) and toluene (15 ml) was refluxed for 24 hr and cooled to room temperature. The toluene solution was washed with water, 0.5N HCl, water, dried over $Na_2SO_4$ and evaporated to dryness under reduced pressure. The crude product was used as is.

Stigmasterol Prednisolone Succinate Diester (SE-24-II)

Stigmasterol prednisolone succinate diester was prepared in the same manner as stigmasterol triethyleneglycol prednisolone diester, substituting stigmasterol succinate monoacid for stigmasterol triethyleneglycol succinate monoacid. The crude product was purified by column chromatography on silica gel eluted with $CH_2Cl_2$, $CH_2Cl_2/EtOAc$, 9:1, 8:2.

Spectral Data Confirming Product Structures

Figure 11:
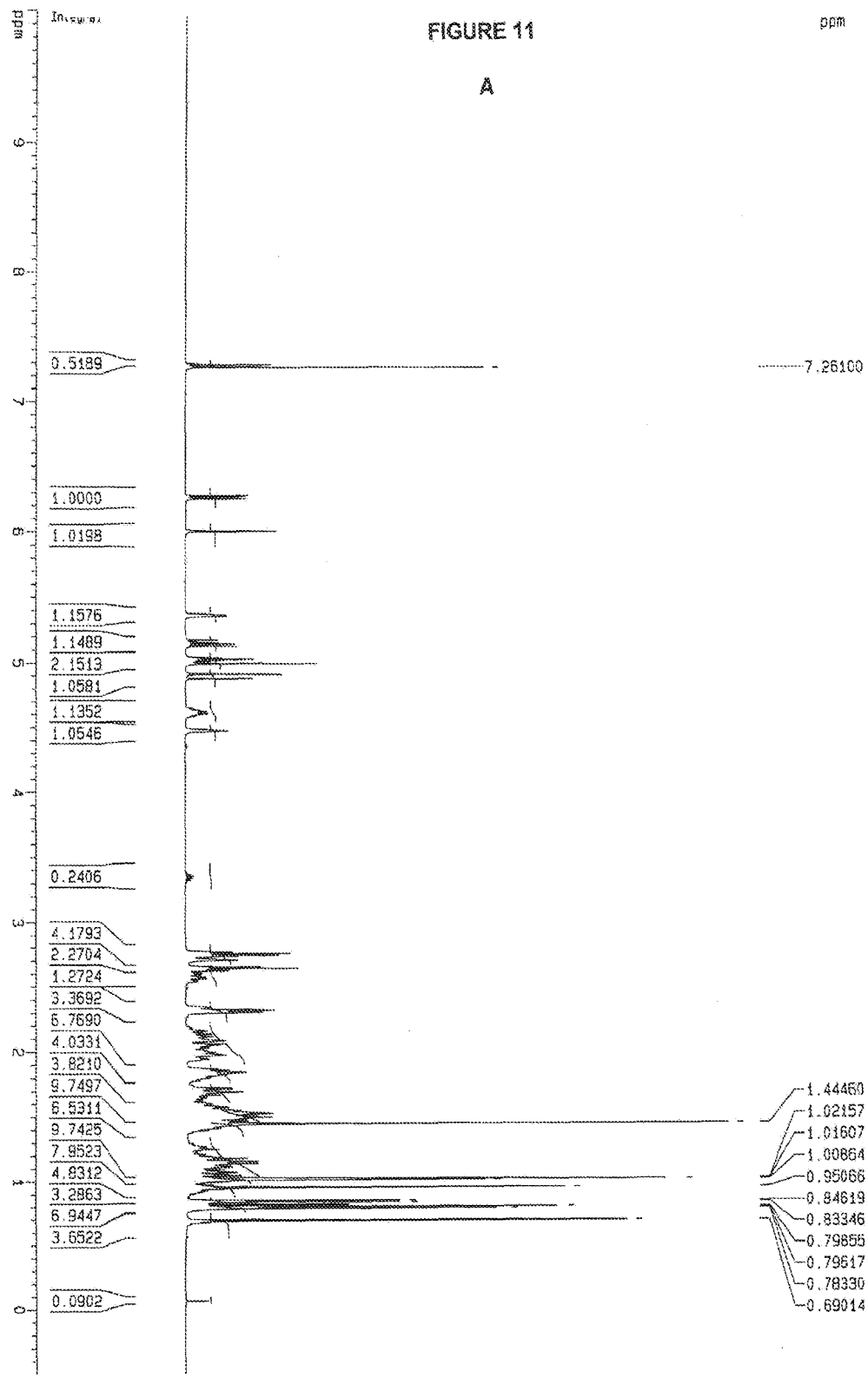
FIGS. 11A-L show the spectral data confirming the structures of SE-24-II (FIGS. 11A-C and J-L), SE-22-II (FIGS. 11D-F and M-O), and SE-41-II (FIGS. 11G-I and P-R).
Figure 11:
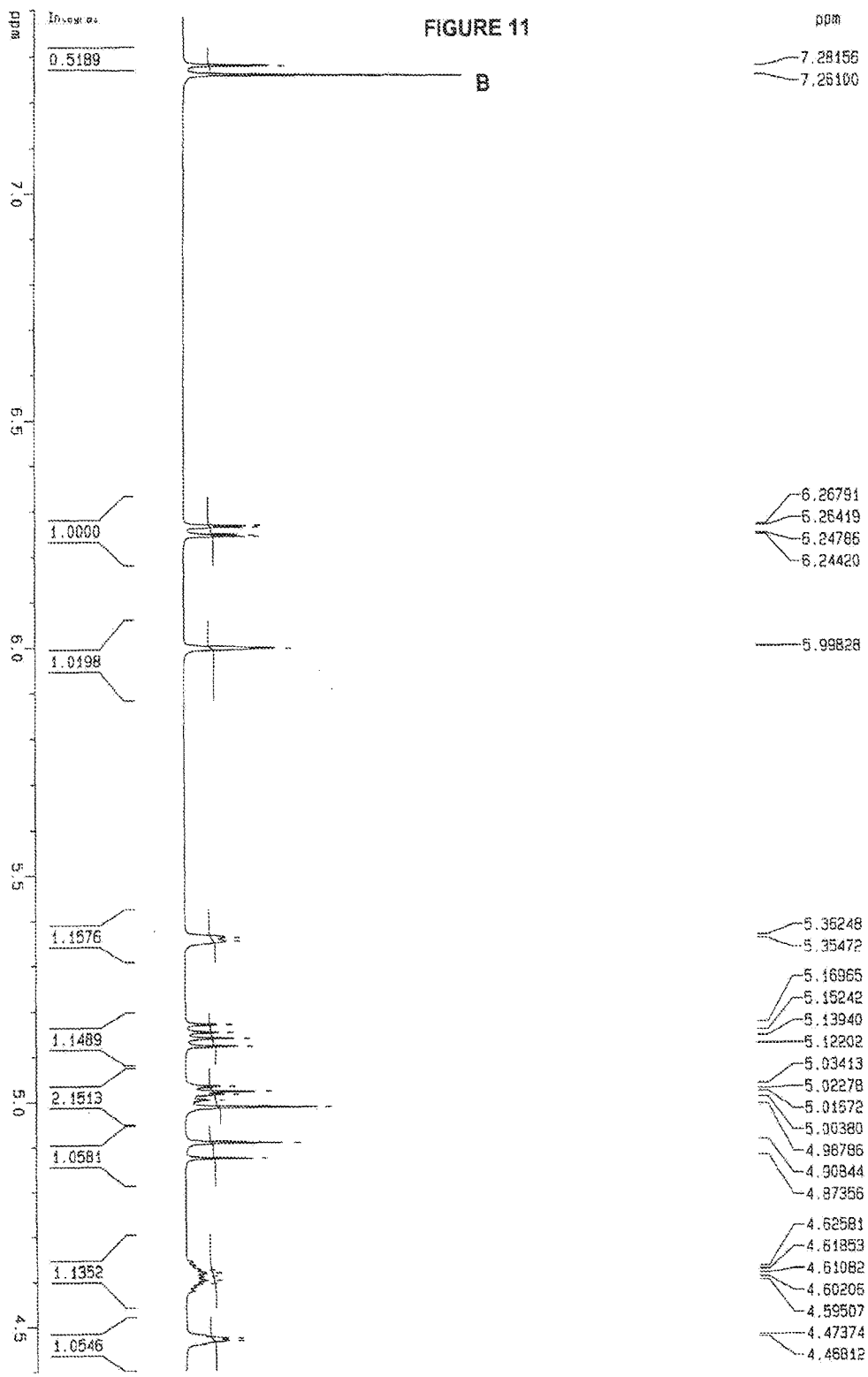
Figure 11:
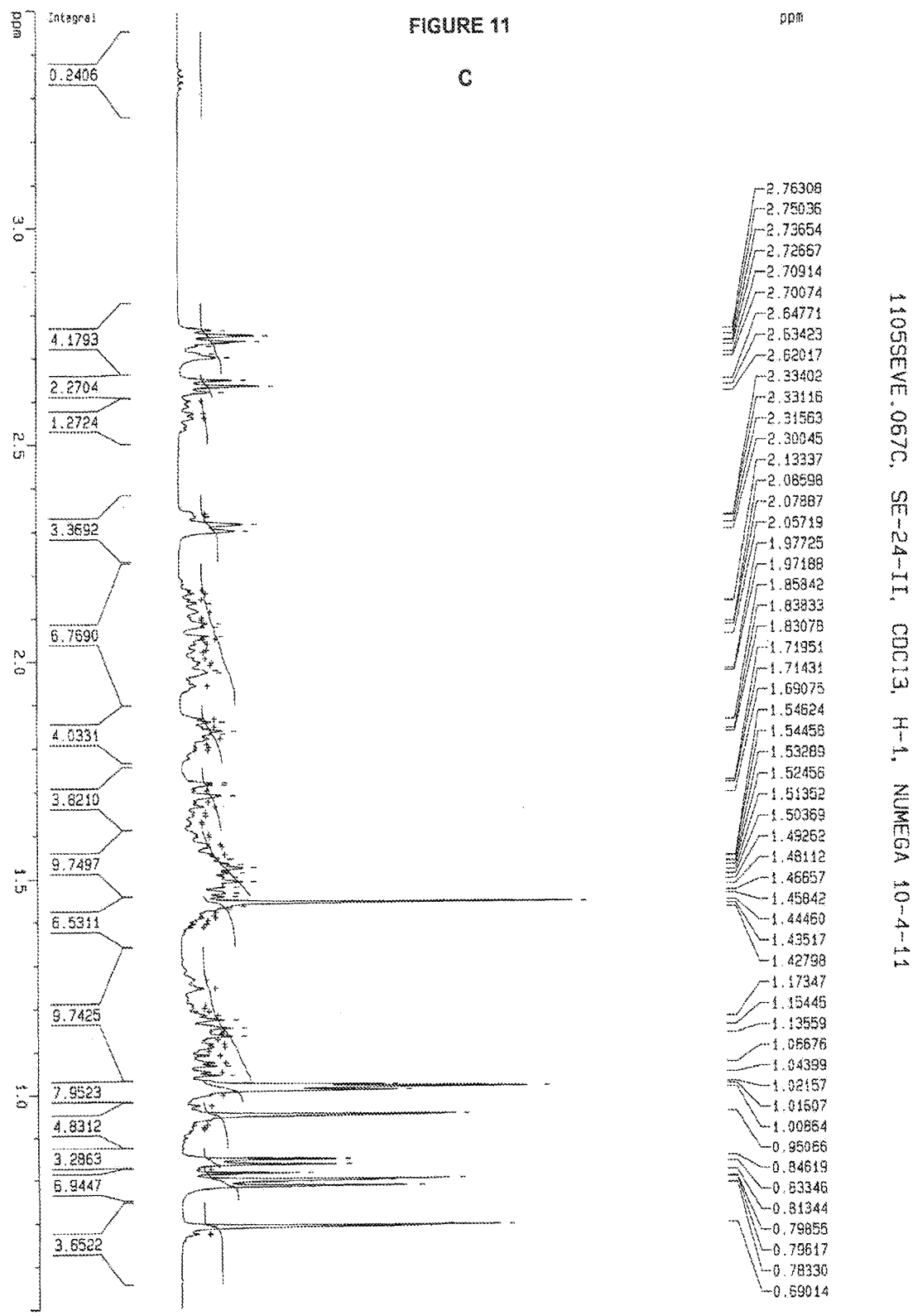
Figure 11:
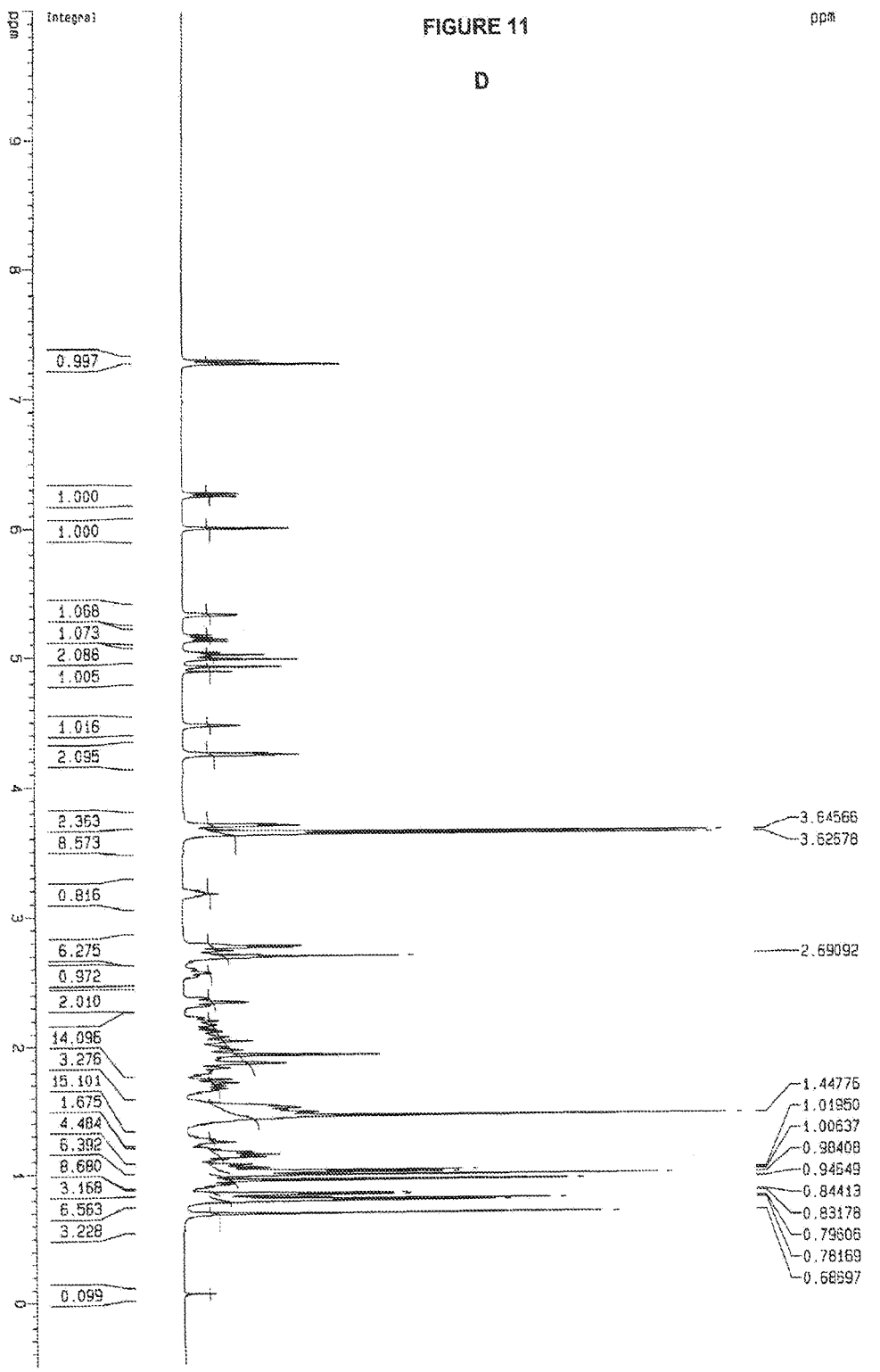
Figure 11:
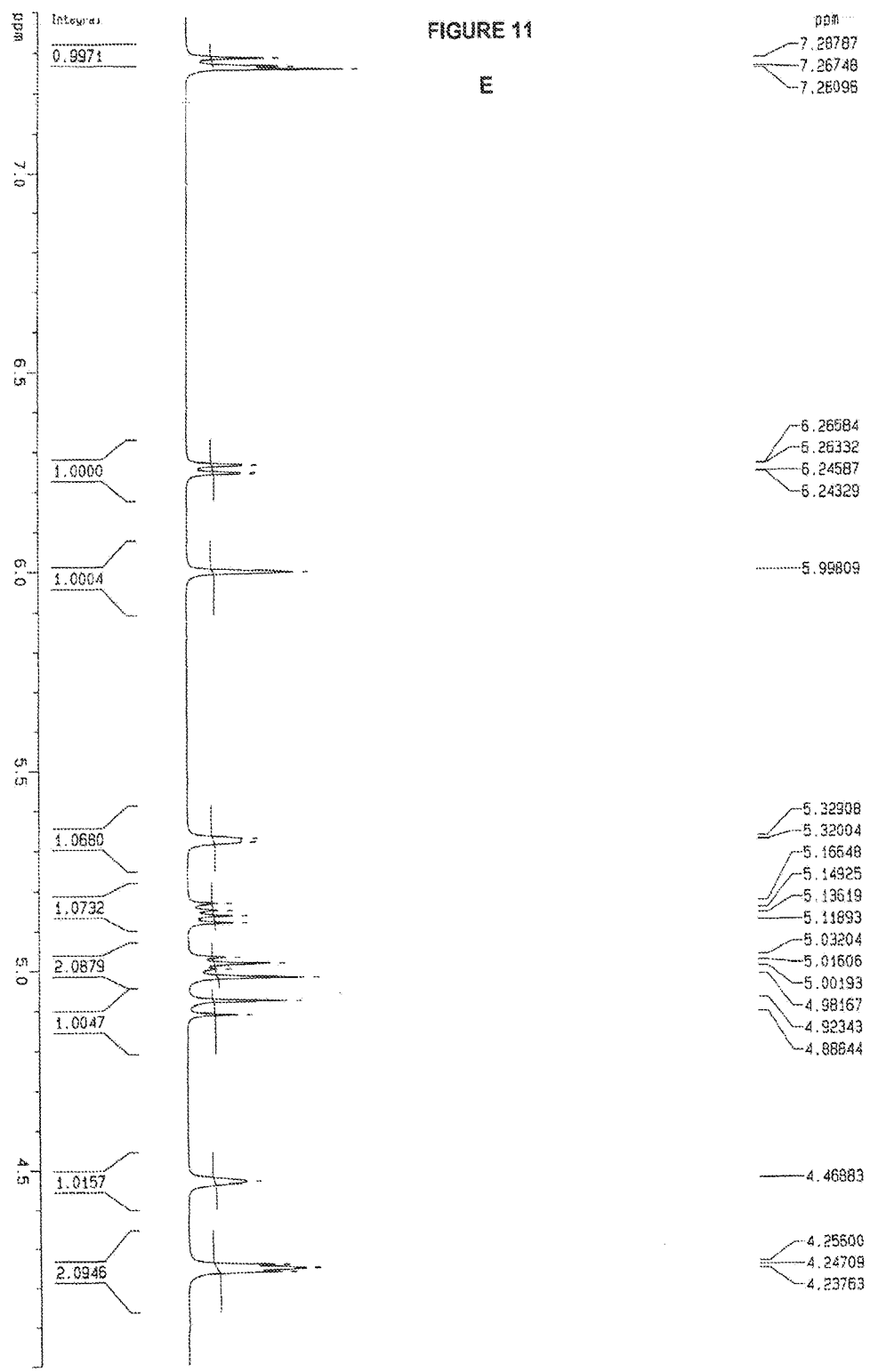
Figure 11:
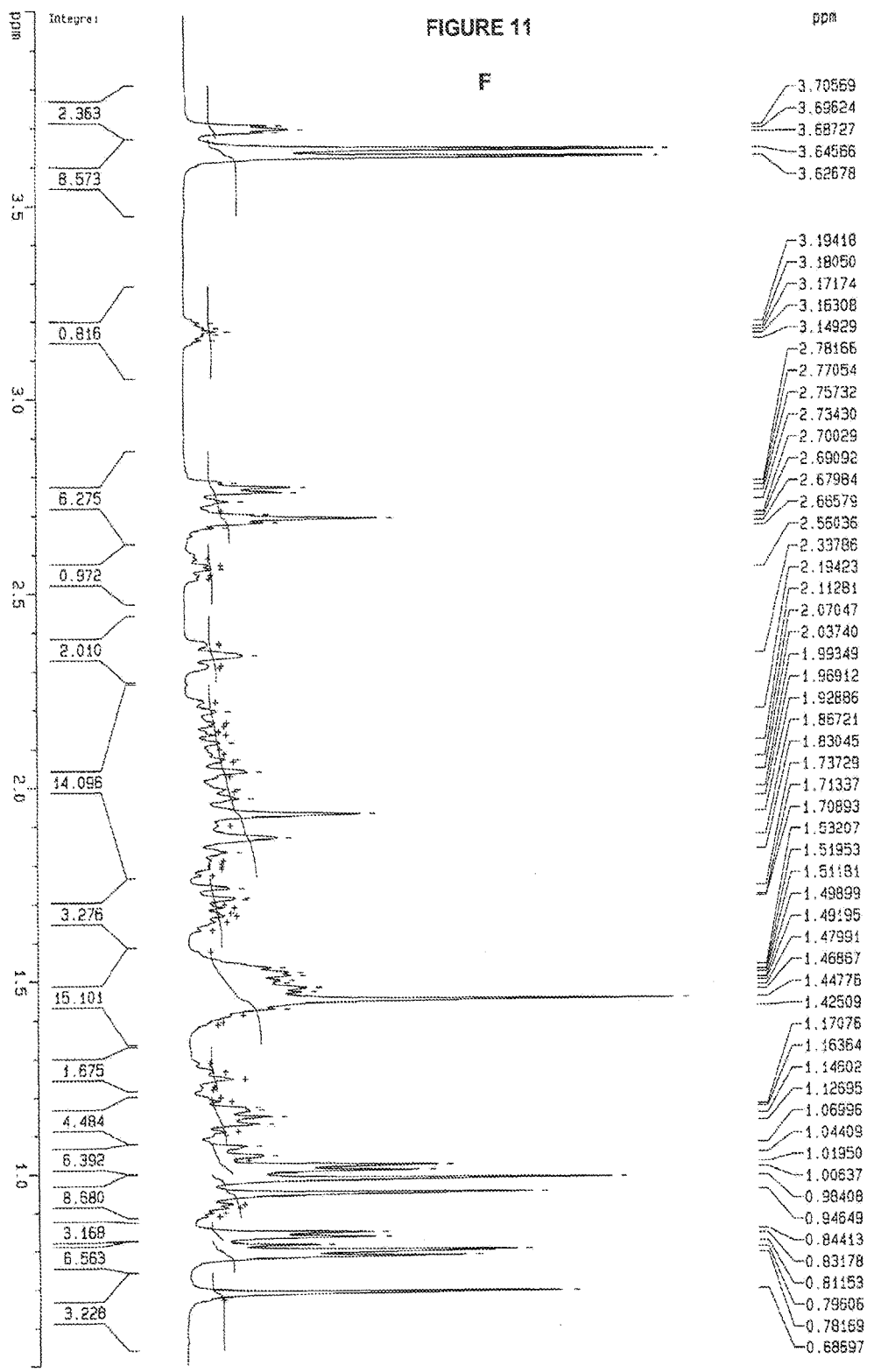
Figure 11:
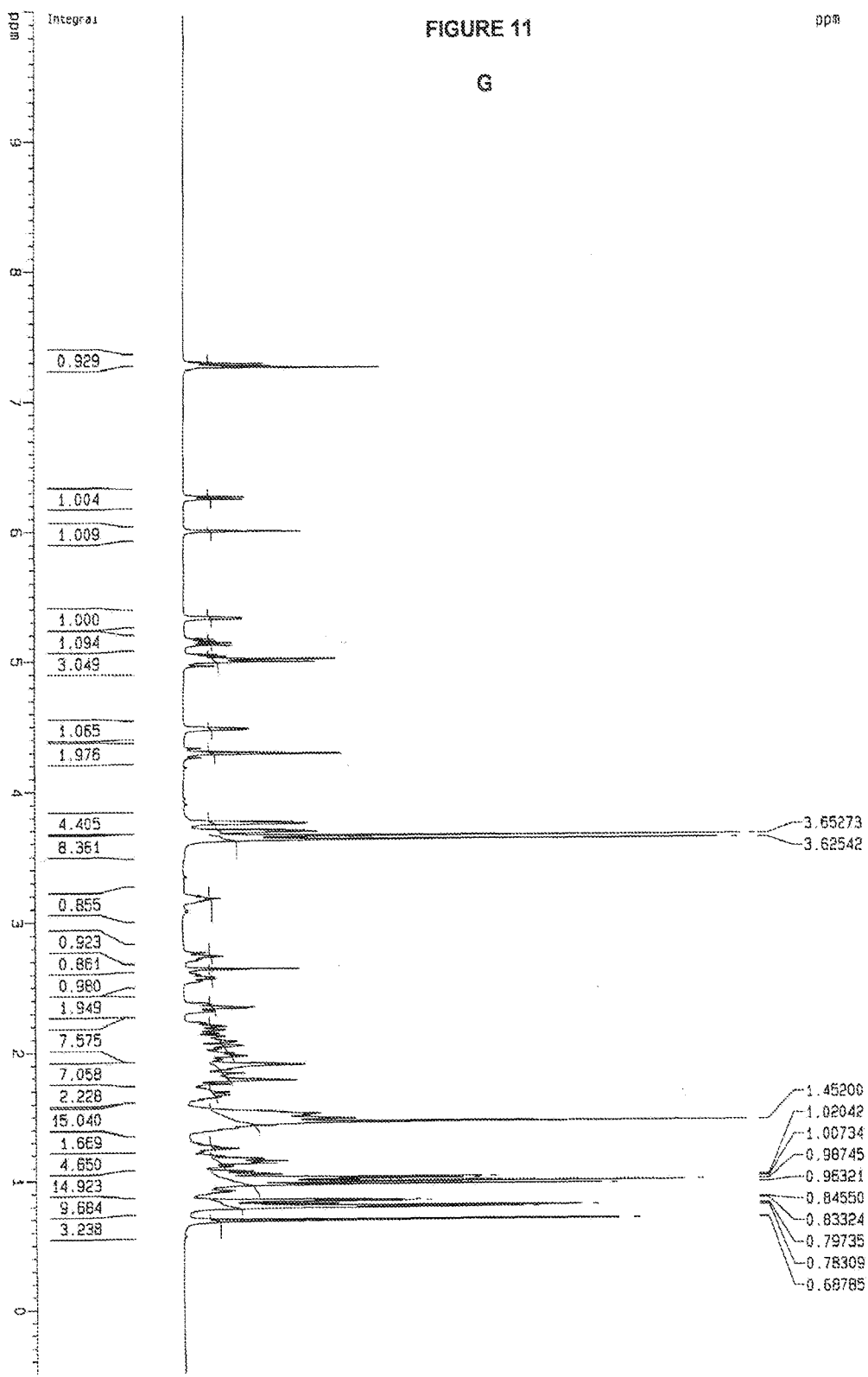
Figure 11:
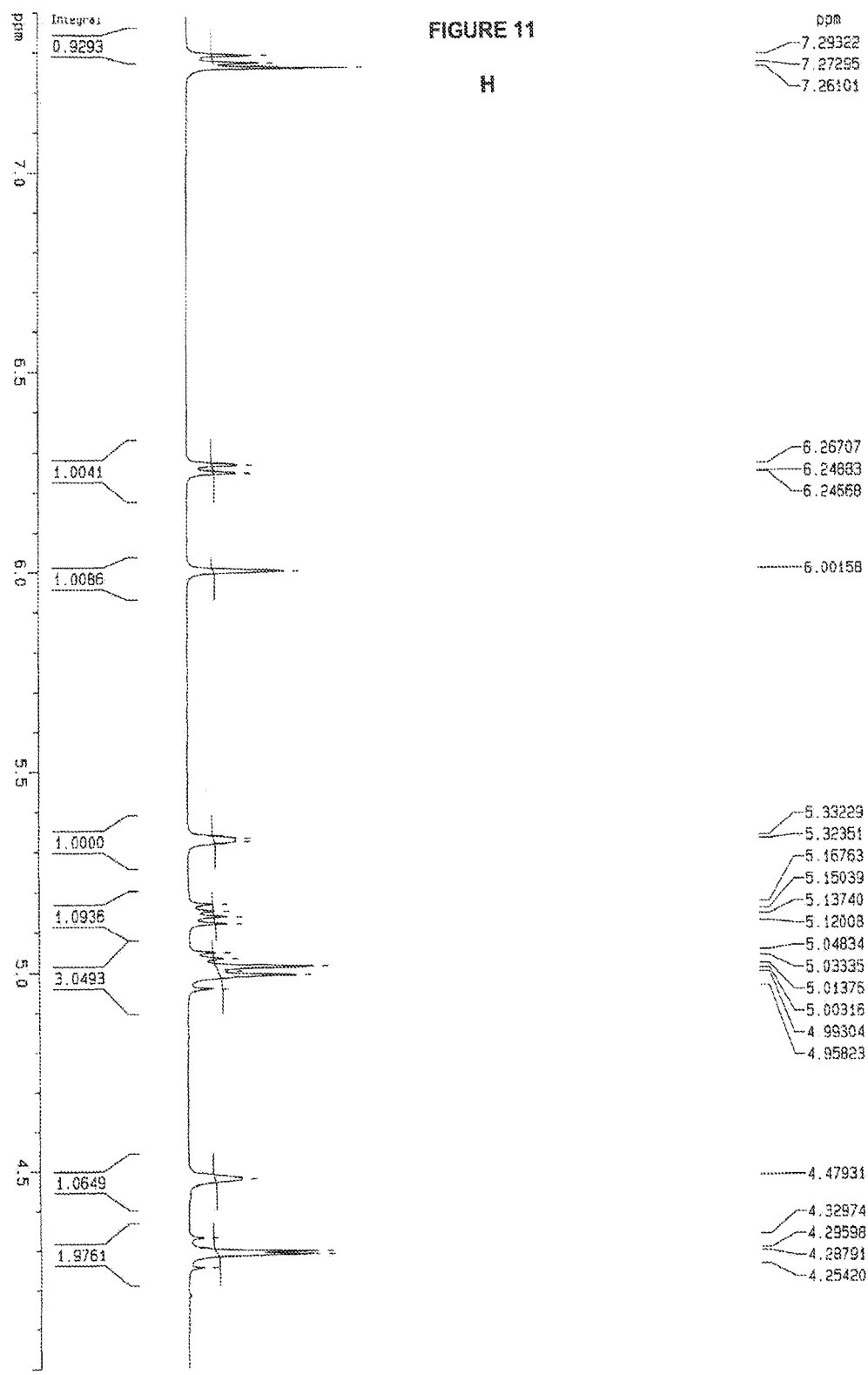
Figure 11:
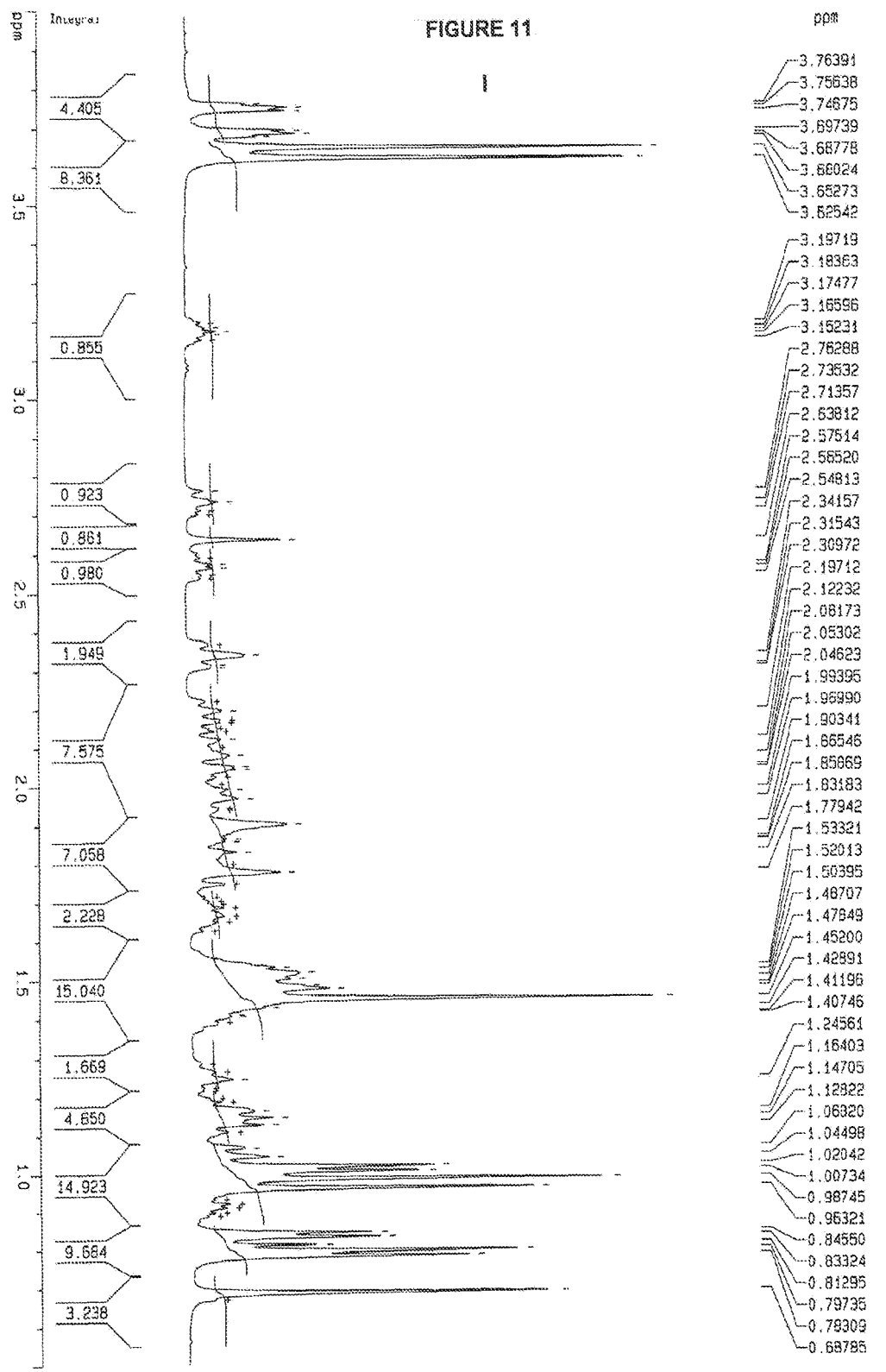
Figure 11:
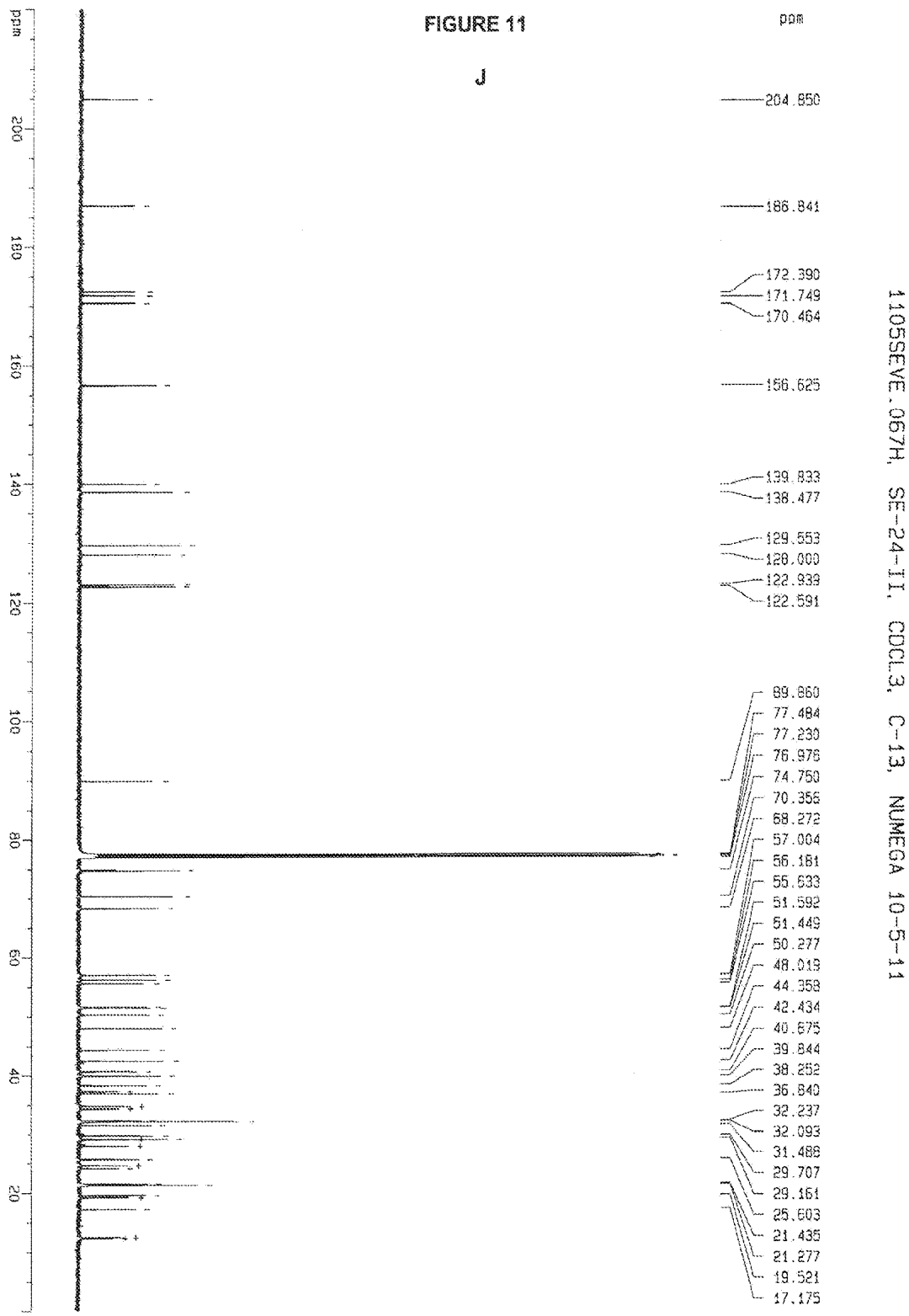
Figure 11:
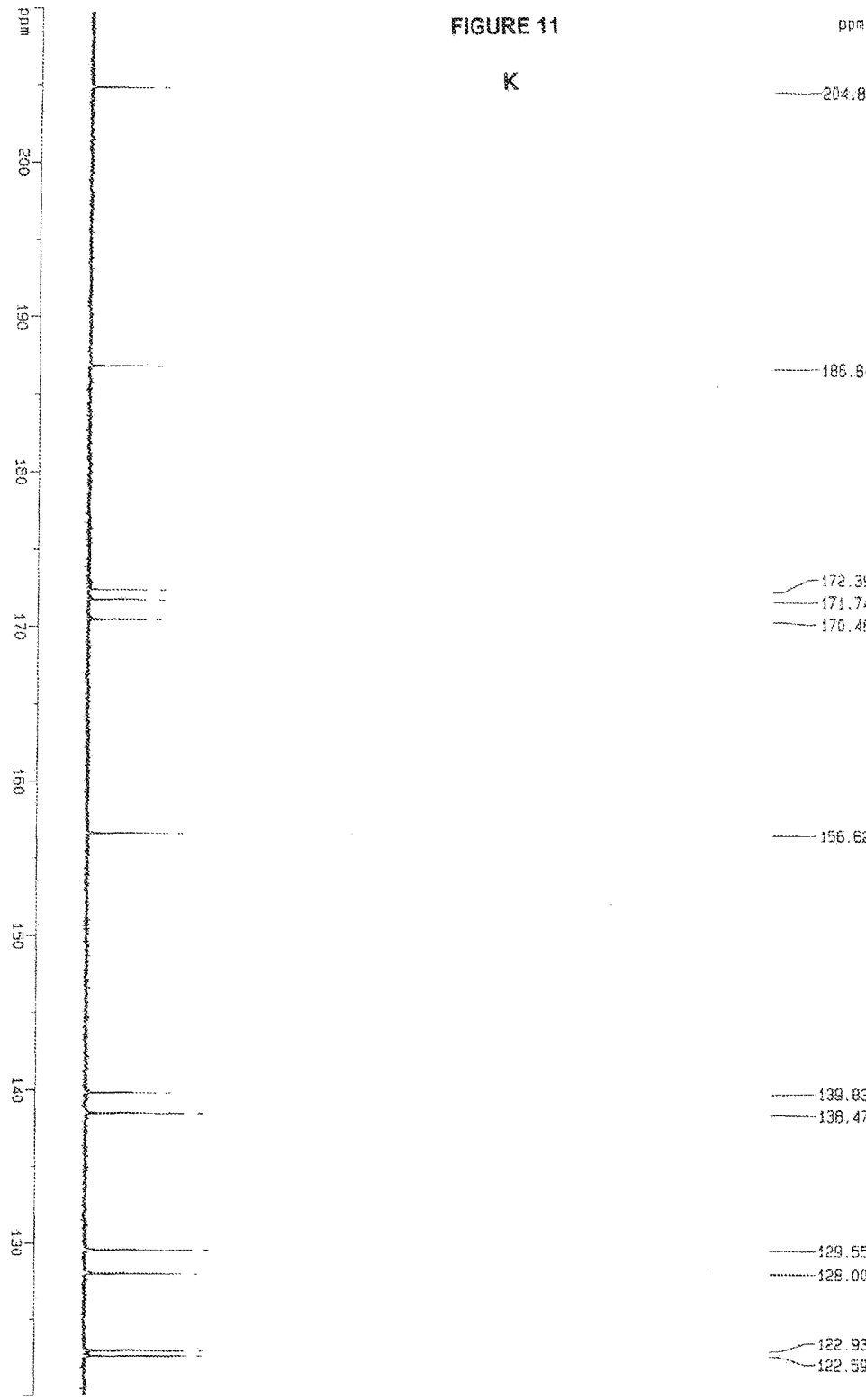
Figure 11:
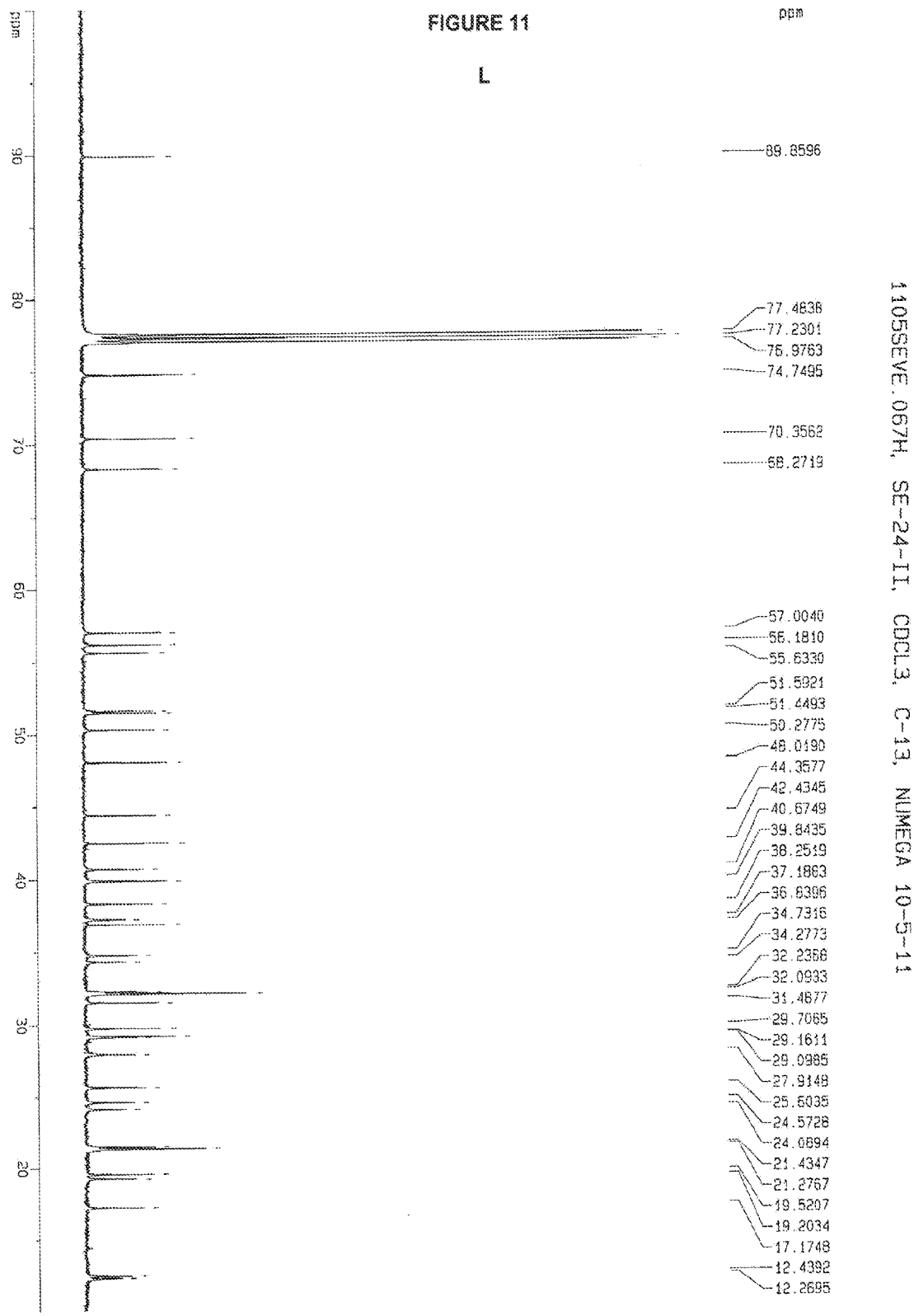
Figure 11:
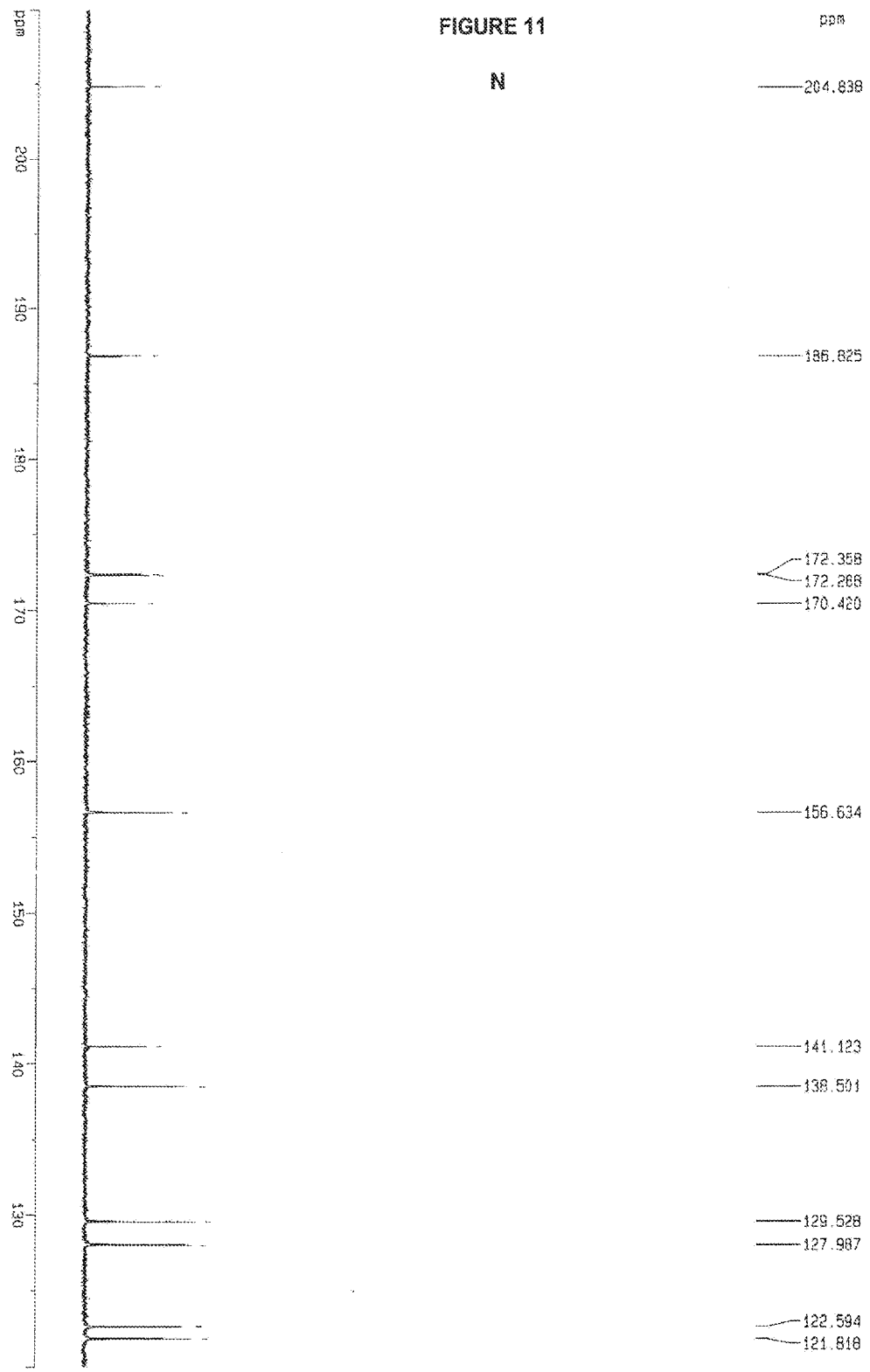
Figure 11:
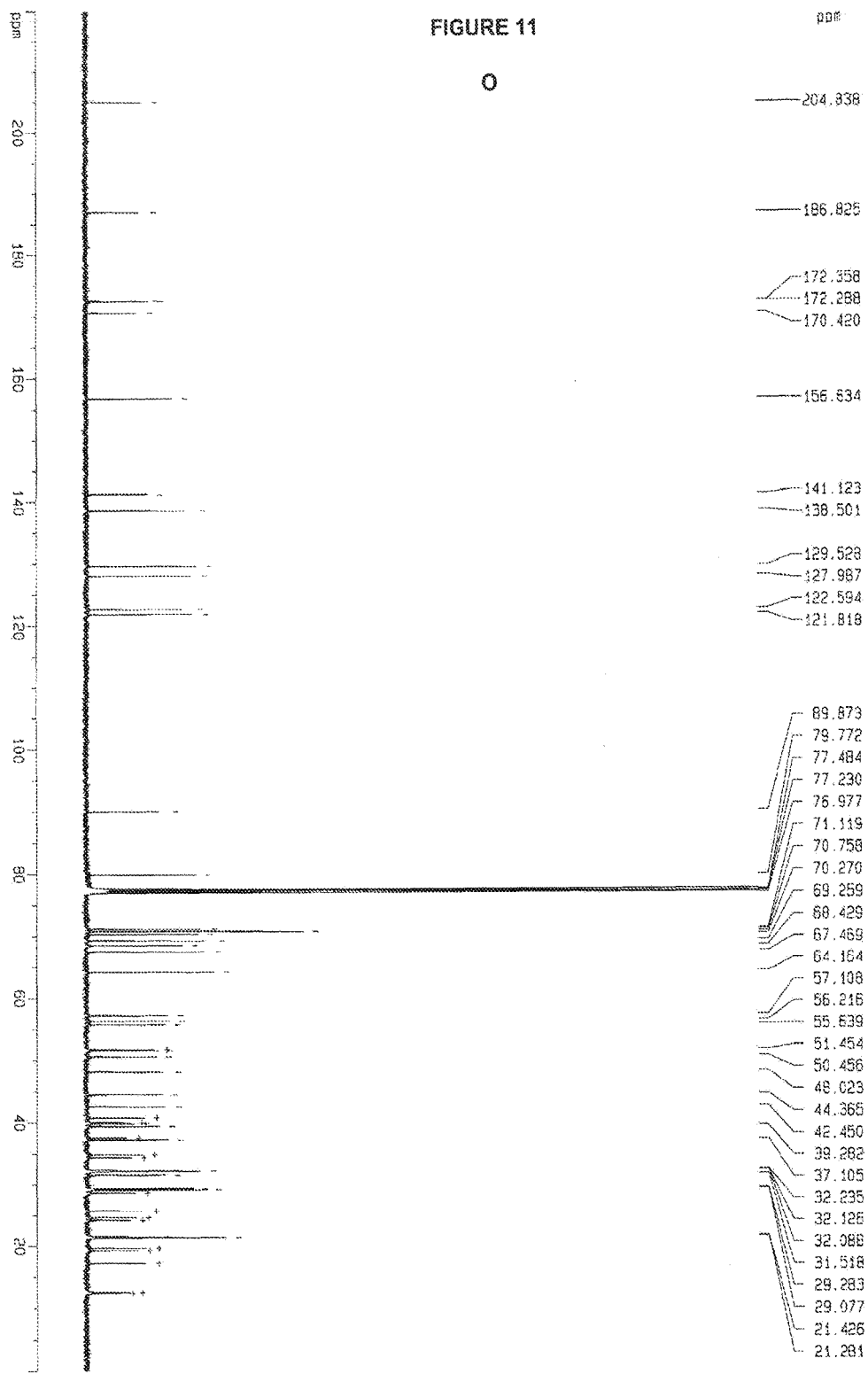
Figure 11:
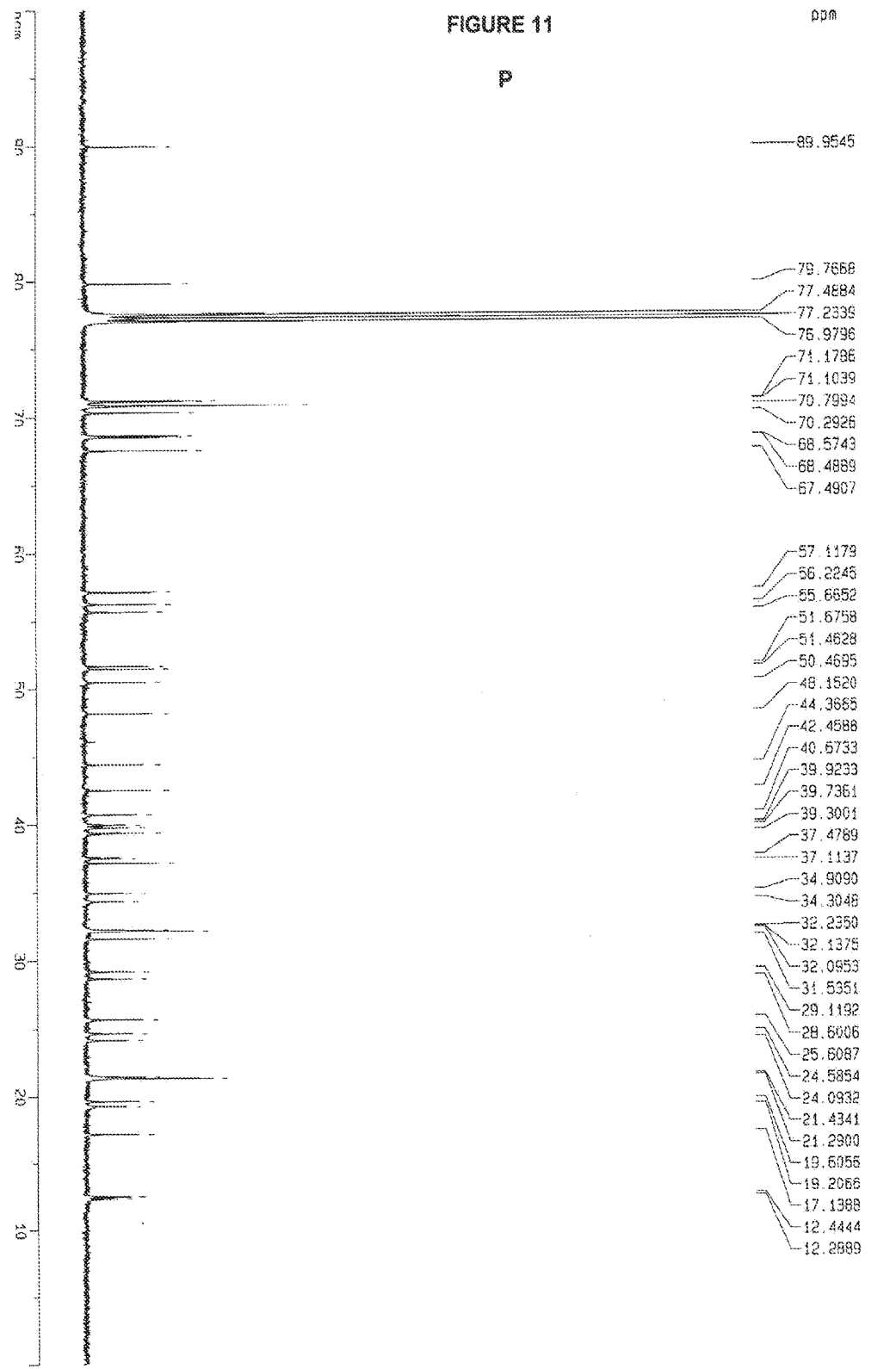
Figure 11:
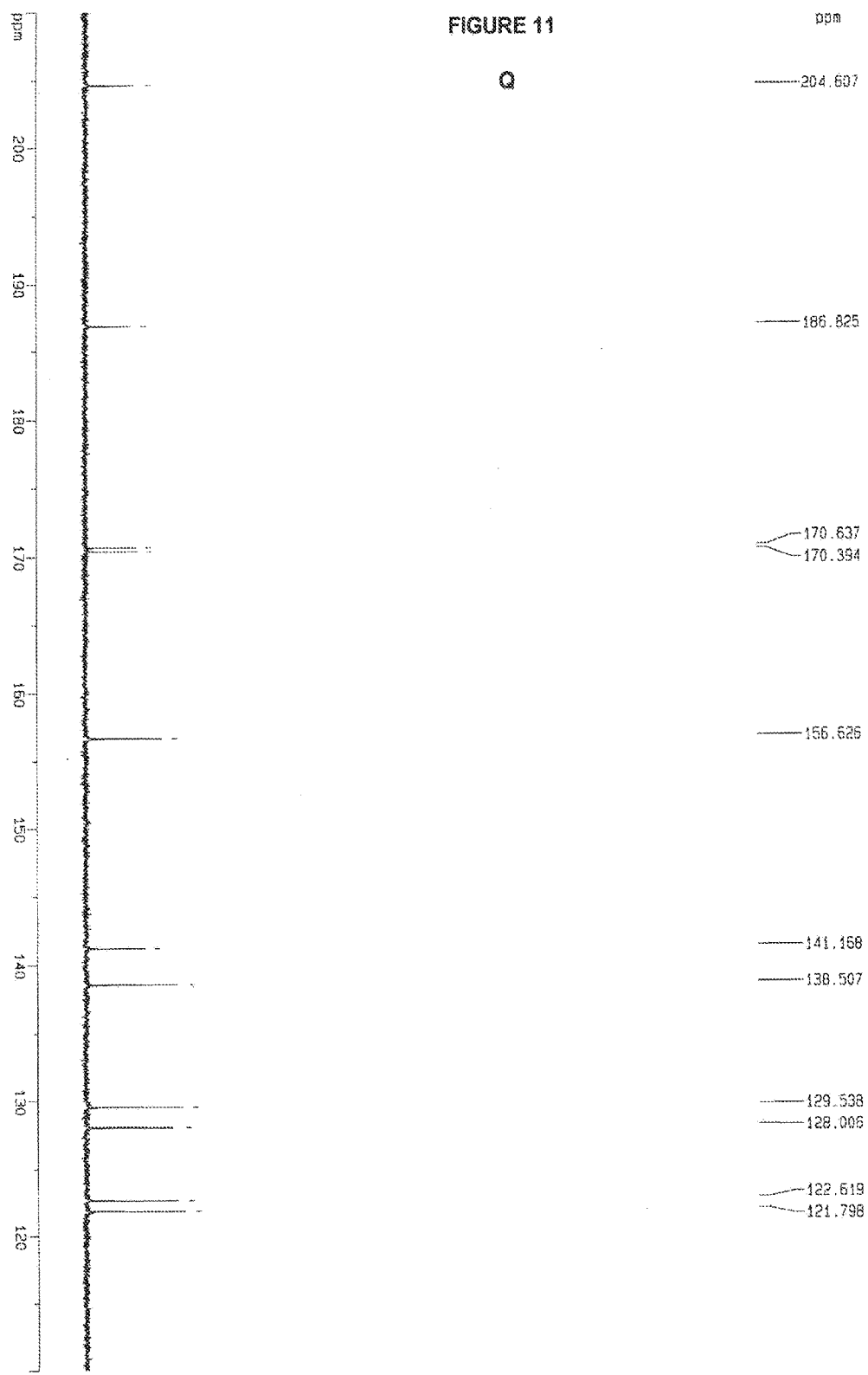
Figure 11:
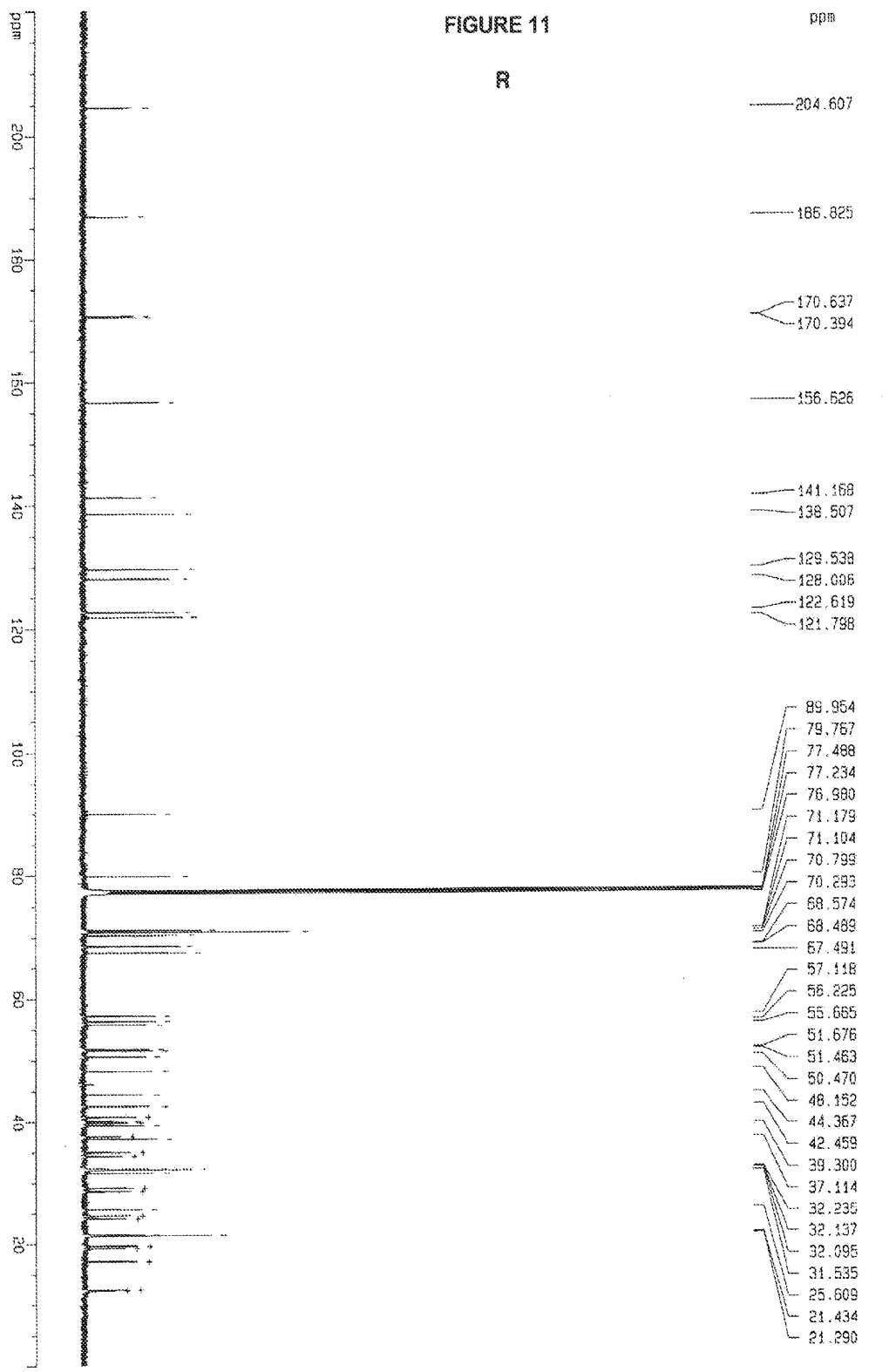

FIGS. 11A-L show the spectral data confirming the structures of SE-24-II (FIGS. 11A-C and J-L), SE-22-II (FIGS. 11D-F and M-O), and SE-41-II (FIGS. 11G-I and P-R).

Example 2

Plant Steroid-Conjugated Prednisone Alter Gene Expression Patterns in a Manner Similar to the Unconjugated Drug This example shows that a plant steroid-conjugated drug that is minimally absorbed systemically can elicit the same potential therapeutic response in intestinal cells as a non-conjugated drug. Specifically prednisone was conjugated to stigmasterol, which is one of the most poorly absorbed plant sterols, to deliver anti-inflammatory effects to intestinal cells without significant systemic absorption. Caco-2 intestinal cells were used. These types of cells have been used as a cell based assay to evaluate the effects of drugs.

Gene expression profiles were generated from 2.5 µM and 25 µM treatments of Caco-2 cells (ATCC). The treatments consisted of a reference compound (prednisone) and three experimental compounds: SE-22-II, SE-24-II and SE-41-II. The active forms of these compounds had formulas 1(o), 1(p) and 1(q), respectively.

All compounds were individually applied to Caco-2 cells (250,000/well). After RNA isolation of each treatment, the isolated RNAs were individually labeled as cDNA probes and applied to Illumina HT-12 array chips. Results from the gene array assays revealed that all compounds (reference and test compounds) affected gene expression compared to non-treated Caco-2 cells. Using the Inforsense Suite of statistical and visualization algorithms (Volcano plots), a broad number of gene classes were observed to be affected by the compound treatments. In particular, for all of the compound treatments tested, >1 fold gene changes were seen in a broad range of genes in a statistically significant manner. A number of genes involved in inflammation, immune system response, cell surface and nuclear hormone signal transduction, fat metabolism and cell cycle/cell differentiation/proliferation were affected. In particular, compounds SE-22 and SE-24 displayed more similar gene profiles to prednisone than did compound SE-41.

Figure 2:
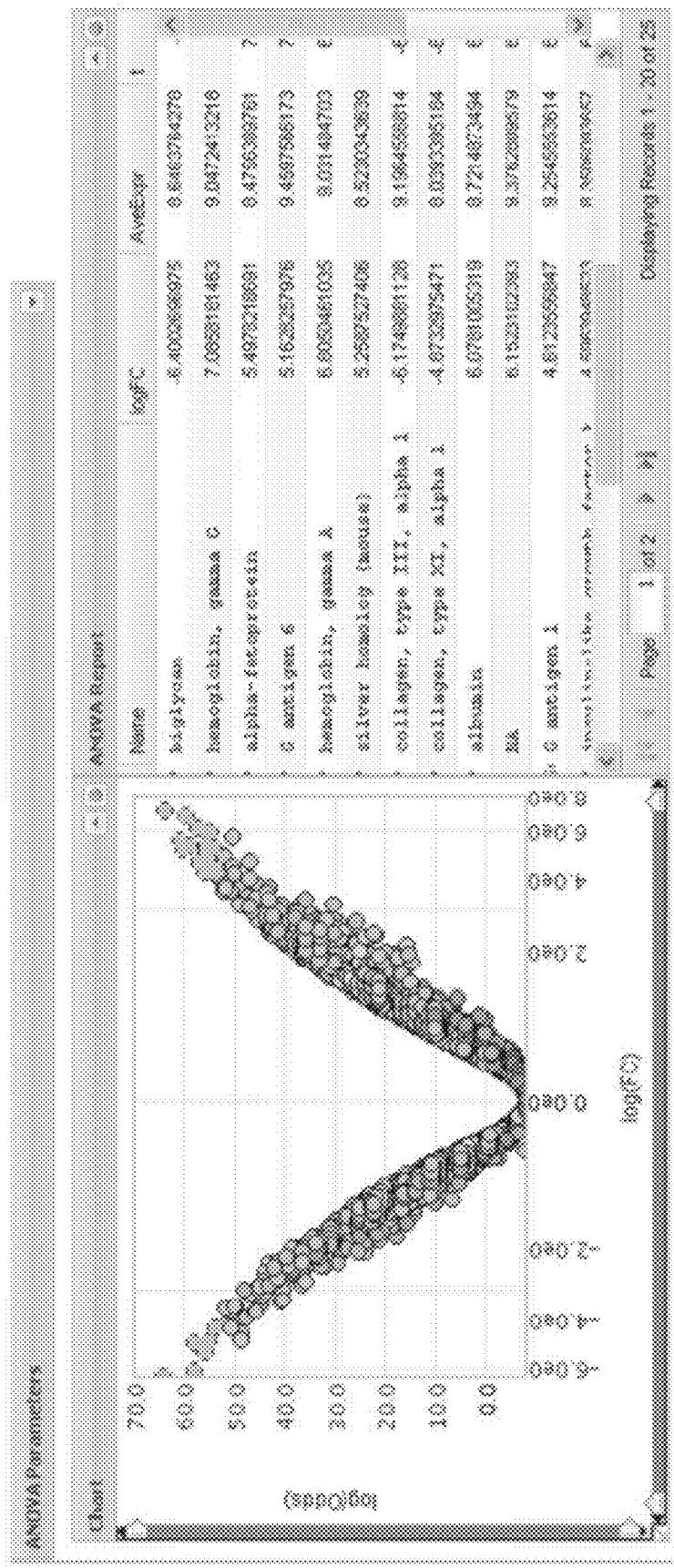
FIG. 2 shows an example of a Volcano plot of gene expression changes associated with treatment of Caco-2 cells with a sterol-conjugated prednisone.
Figure 3H:
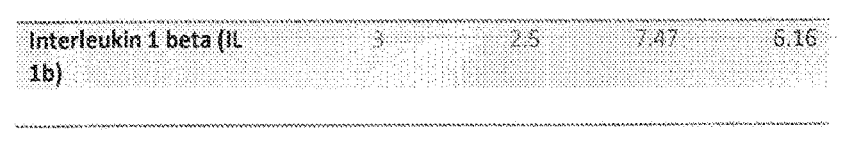

Key Genes Affected per Gene Class: Using the Inforsense Suite of Data Analysis tool (IDBS), a total of 36 Volcano plots were generated against 36 gene array assays (triplicate array assays per nontreatment and treatment of compounds). Volcano plots were generated for each compound data set to statistically identify key genes upregulated and down regulated (see example in FIG. 2). From the volcano plots for each array experiment the most pronounced upregulated and down-regulated genes were identified. Genes were identified on both sides of the volcano plots (shaded in gray in FIG. 2) that were at a correlation coefficient of p<0.05. Genes identified in this manner are listed in FIGS. 3A-F for Caco-2 cells treated with 2.5 µM of each compound. It was also found that the 25 µM treatments demonstrated cytotoxic effects on the gene expression profiles. In addition, 2.5 µM treatments exhibited a far greater linear (dose-dependent) response when looking at several key genes affected in the profiles (e.g., HNF-4, Glypican, and Phosphoenolpyruvate carboxykinase 1).

Methods

1. Cell Culture: Caco-2 Cells Treated with Compound Set

The human colon adenocarcinoma cell line Caco-2 was cultured in Dulbecco's Modified Eagle's Medium (Sigma-Aldrich) with 4.5 g/l glucose, L-glutamine, $NaHCO_3$ and pyridoxine HCl supplemented with 1% (vol/vol) nonessential amino acids, 1% Na-pyruvate, 1% penicillin/streptomycin, and 10% (vol/vol) heat inactivated fetal calf serum, all purchased from Gibco BRL. Cell cultures were transferred weekly by trypsinization and incubated at 37° C. in a humidified incubator containing 5% $CO_2$. After 4 weeks of cell culture, prednisone, SE-22-II, SE-24-II and SE-41-II were each added to separate triplicate wells (250,000 cells/well) at final effective concentrations of 2.5 µM and 25 µM, respectively. Cells were exposed to each compound, respectively, for 24 hours.

2. Cell Harvest and RNA Isolation

Total RNA was isolated according to the TRIzol manufacturer's instructions (Invitrogen). RNA quality was assessed with a 2100 Bioanalyzer (Agilent). RNA from pooled triplicates of the various cell treatments, all with an RNA integrity number >7, was further purified with Qiagen RNeasy columns. From 300 ng of total RNA, the Illumina TotalPrep RNA Amplification kit (Ambion) was used to generate amplified biotinylated cRNA after reverse transcription by the Eberwine procedure. cRNA (900 ng) was hybridized overnight to Illumina HT-12 BeadArrays, which were then washed and stained with streptavidin-Cy3 (Amersham-Pharmacia Biotech) according to the Illumina protocol. Arrays were scanned on a BeadArray Reader (Illumina).

Specific transcripts within the biotinylated cRNA were measured by fluorescent imaging after direct hybridization to HT-12 bead arrays, which contain 12 arrays per slide, each with an average of 15 beads for each of 48,803 probes measuring 37,846 annotated genes and additional transcripts. Raw measurements of the intensity of each bead were captured directly and processed as "bead-level" for the samples, as described below. For both treated and non-treated samples, measurements were processed as "probe-level" data by GenomeStudio software (Illumina). The software checked that a probe had ≥3 beads present on the array (if not, the probe was considered to be missing), did a local background subtraction for each bead, and then condensed bead-level data to a single probe-level value per probe by removing outliers that were >3 median absolute deviations from the median, recalculating the mean of the remaining values. Raw probe-level values were extracted from the software, without the use of its correction or normalization options, but with the use of its option for imputing missing values.

3. Data Analysis

ANOVA statistical analysis was performed on all Illumina gene expression array files. Volcano plots were generated for all pooled bead array data using Inforsense 5.1 Suite (IDBS).

4. Results

Figure 4:
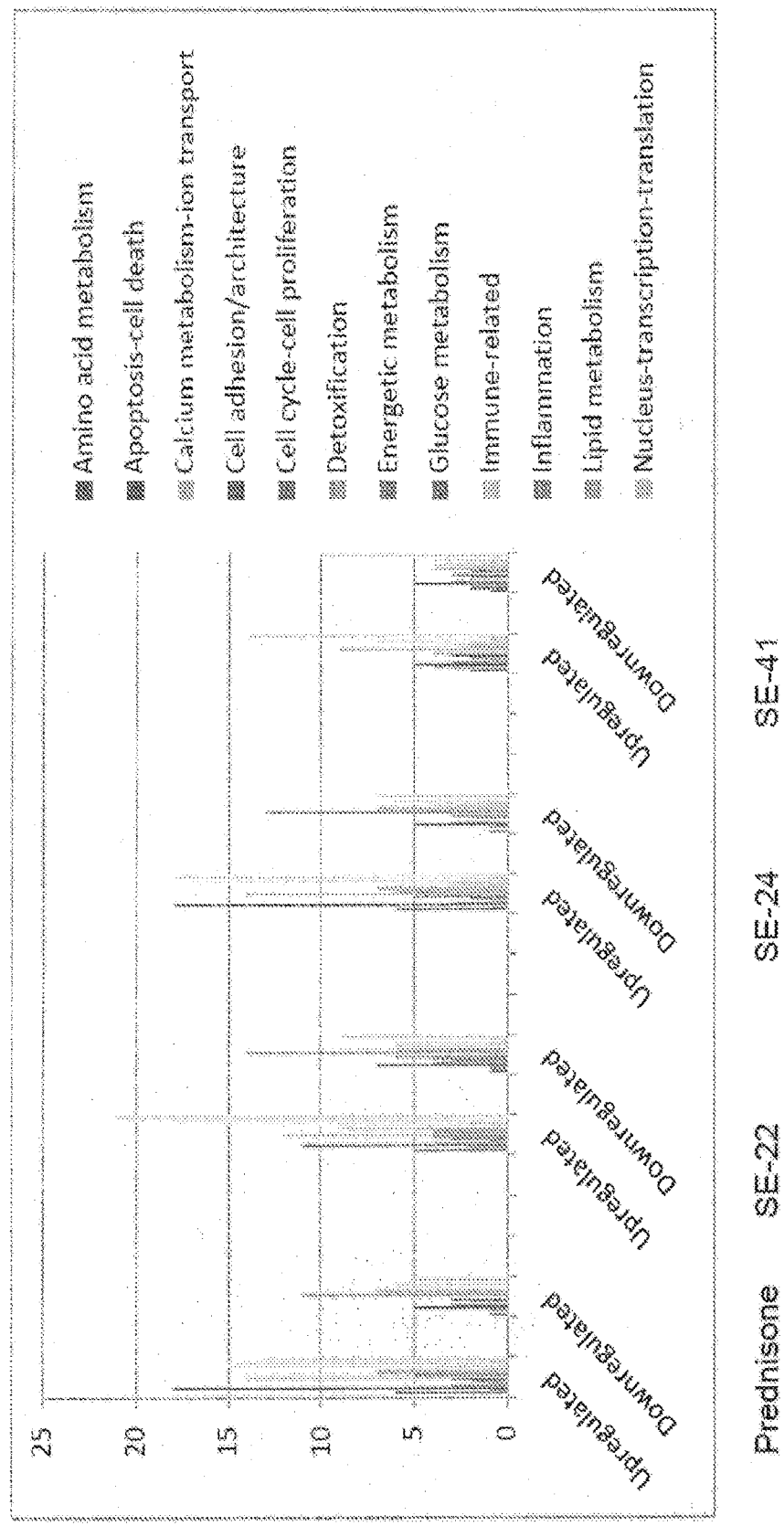
FIG. 4 shows the gene response of key gene families to 2.5 μM of Prednisone, SE-22-II, SE-24-II and SE-41-II.

FIG. 4 shows the gene response of key gene families to 2.5 µM of prednisone, SE-22-II, SE-24-II and SE-41-II.

5. Discussion

Figure 5:
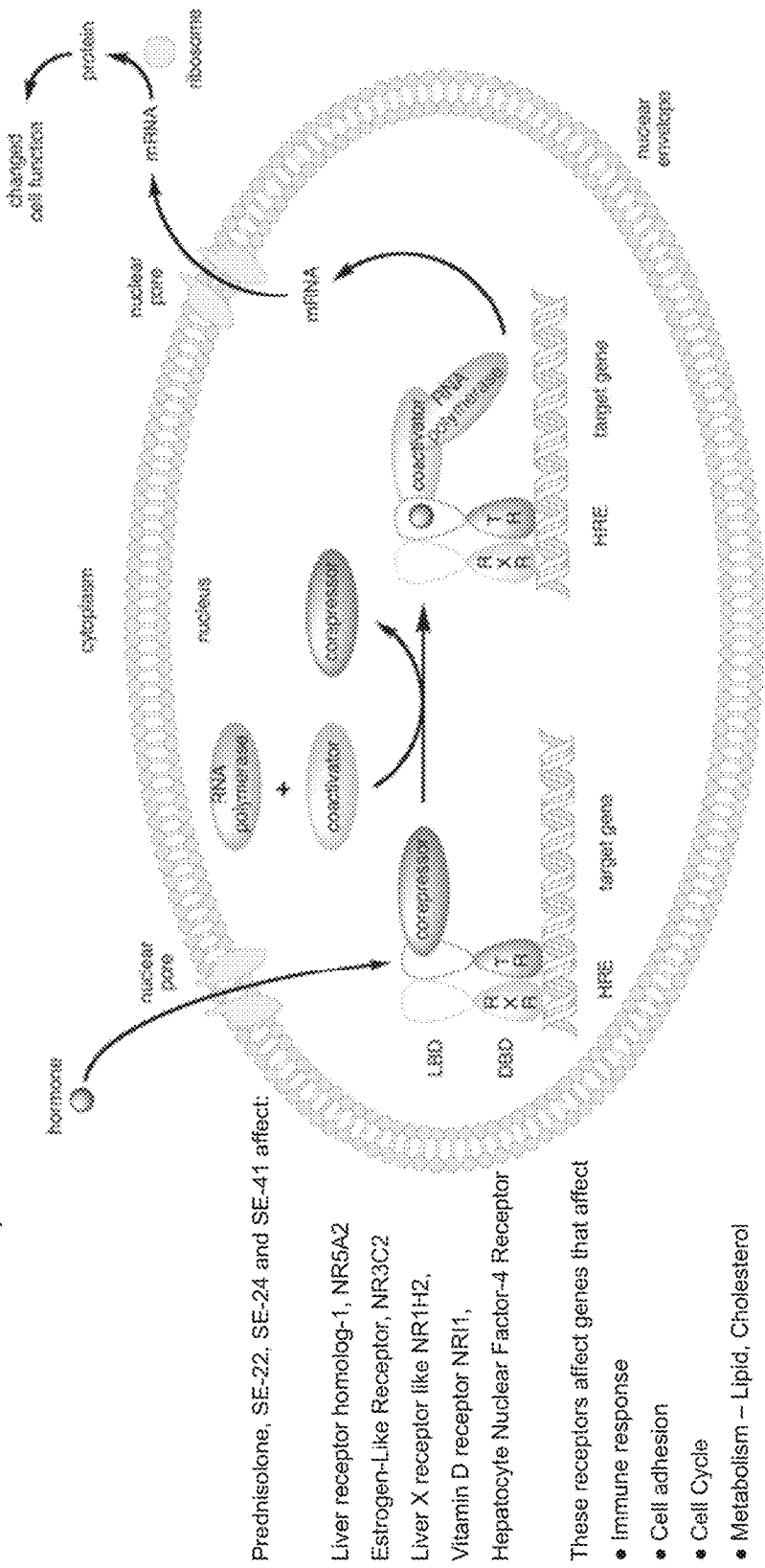
FIG. 5 shows nuclear hormone receptors, which are affected by prednisolone, SE-22, SE-24, and SE-41.
Figure 6:
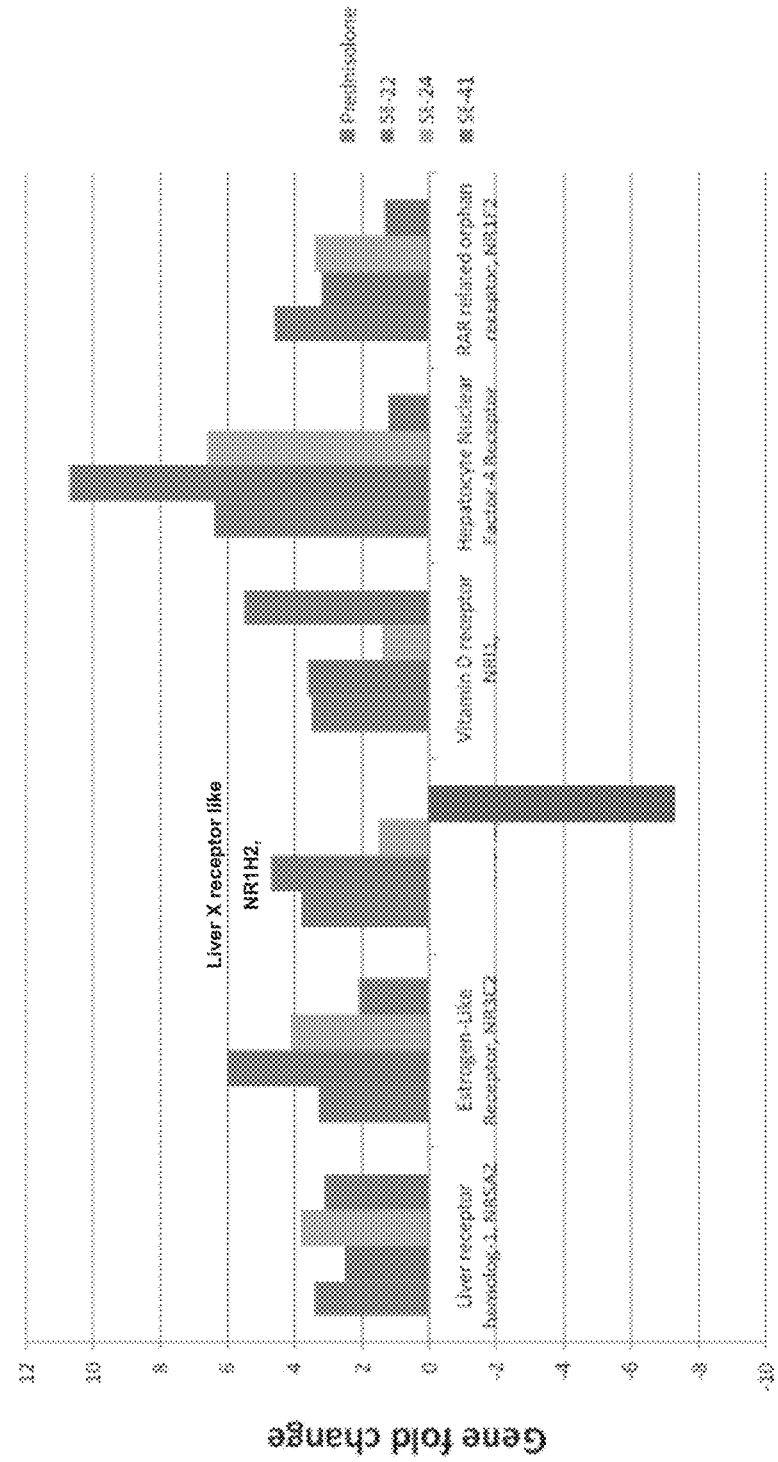
FIG. 6 shows gene responses that affect nuclear hormone receptors in Caco-2 cells.

Caco-2 cells were treated with various test compounds (prednisone, SE-22-II, SE-24-II, and SE-41-II), and results were compared to the results from cells treated with prednisolone. Non-treated and treated cells were assessed for their gene expression profiles after 2.5 µM and 25 µM drug treatments (after 24 hours). The Caco-2 cells demonstrated consistent results within replicates of each 2.5 µM treatment as compared to the 25 µM treatment. All of the compounds tested exhibited bioactivity. One hundred and thirty genes demonstrated a statistically significant >1-fold response ($p<0.005$). The key classes of genes affected included inflammation, immune system, nuclear-transcription-translation, and cell adhesion. Up- and down-regulation of multiple genes associated with prednisolone exposure may depend on the presence of specific transcription factors and/or transcription factor binding motifs (TFBMs) in the promoter regions of the genes affected. In particular, the highest levels of gene responses (>3.0 fold gene expression level change) were seen for nuclear hormone receptor (see schematic in FIG. 5), cytokine and chemokine receptor genes and their corresponding receptors. FIG. 6 shows gene responses that affect nuclear hormone receptors in Caco-2 cells.

In the gene profiling assays described herein, specific nuclear hormone receptor genes were affected across all of the compounds tested. Specifically, up- and down-regulation effects were seen for several genes of this class (e.g., Liver receptor homolog-1, NR5A2, Estrogen-Like Receptor NR3C2, Liver X receptor-like NR1H2, Vitamin D receptor NRI1, RAR-related orphan receptor, NR1F2, and Hepatocyte Nuclear Factor-4 Receptor). The protein factors of these genes may have broad affects on a broad array of target genes involved in cell cycle, immune function, cell adhesion and metabolism.

Nuclear Hormone Receptors

Nuclear receptors are grouped into a large superfamily and are thought to be evolutionarily derived from a common ancestor. A list of classical and orphan hormone receptors and their ligands is shown in FIG. 7. Evolutionary analysis of the receptors has led to a subdivisionin six different subfamilies. One large family is formed by thyroid hormone receptors (TRs), retinoic acid receptors (RARs), vitamin D receptors (VDRs) and peroxisome proliferator-activated receptors (PPARs), as well as different orphan receptors. Ligands for some of these receptors have been recently identified (see FIG. 7). The second subfamily contains the retinoid X receptors (RXRs) together with chicken ovalbumin upstream stimulators (COUPs), hepatocyte nuclear factor 4 (HNF4), testis receptors (TR2) and receptors involved in eye development (TLX and PNR). RXRs bind 9-cis-retinoic acid and play an important role in nuclear receptor signaling, as they are partners for different receptors that bind as heterodimers to DNA. Ligands for other receptors have not been identified, whereas long-chain fatty acid acyl-CoA thioesters may be endogenous ligands for HNF4. The third family is formed by the steroid receptors and the highly related orphan receptors estrogen-related receptors (ERRs). The fourth, fifth, and sixth subfamilies contain the orphan receptors NGFI-B, FTZ-1/SF-1, and GCNF, respectively. Most subfamilies appear to be ancient since they have an arthropod homolog, with the exception of steroid receptors that have no known homologs. It has been suggested that the ancestral receptors were constitutive homodimeric transcription factors that evolved to independently acquire the ability to bind a ligand and to heterodimerize. However, the possibility that the ancestral receptor was ligand dependent and that mutations changed the ligand-binding specificity or led to loss of ligand binding during evolution cannot be ruled out.

Members of this class of receptors are found in number of tissue types (liver, intestine, brain). Nuclear receptors bind to ligands in the cytosol (Class I) or in the nucleus (Class II). Prior to binding to sterols some members of the nuclear hormone receptor family are bound in an inactive state to other protein factors (e.g., heat shock proteins (chaperonins)), once bound to the sterol, nuclear hormone receptors can then bind as homo or hetrodimers. The activated nuclear hormone receptor (homo or heterodimer) then binds to hormone response elements (HREs) in target genes. Once bound, these genes can be transcriptionally or translationally up or down regulated.

Like other transcriptional regulators, nuclear receptors exhibit a modular structure with different regions corresponding to autonomous functional domains that can be interchanged between related receptors without loss of function. A typical nuclear receptor consists of a variable NH2-terminal region (A/B), a conserved DNA binding domain (DBD) or region C, a linker region D, and a conserved E region that contains the ligand binding domain (LBD). Some receptors contain also a COOH terminal region (F) of unknown function. A schematic of a nuclear receptor is shown in FIG. 8. The receptors also contain regions required for transcriptional activation. The hypervariable A/F region of many receptors contains an autonomous transcriptional activation function, referred to as AF-1, that contributes to constitutive ligand independent activation by the receptor. A second transcriptional activation domain, termed AF-2, is located in the COOH terminus of the LBD, but unlike the AF-1 domain, the AF-2 is strictly ligand dependent and conserved among members of the nuclear receptor superfamily.

Interleukins

Figure 10:
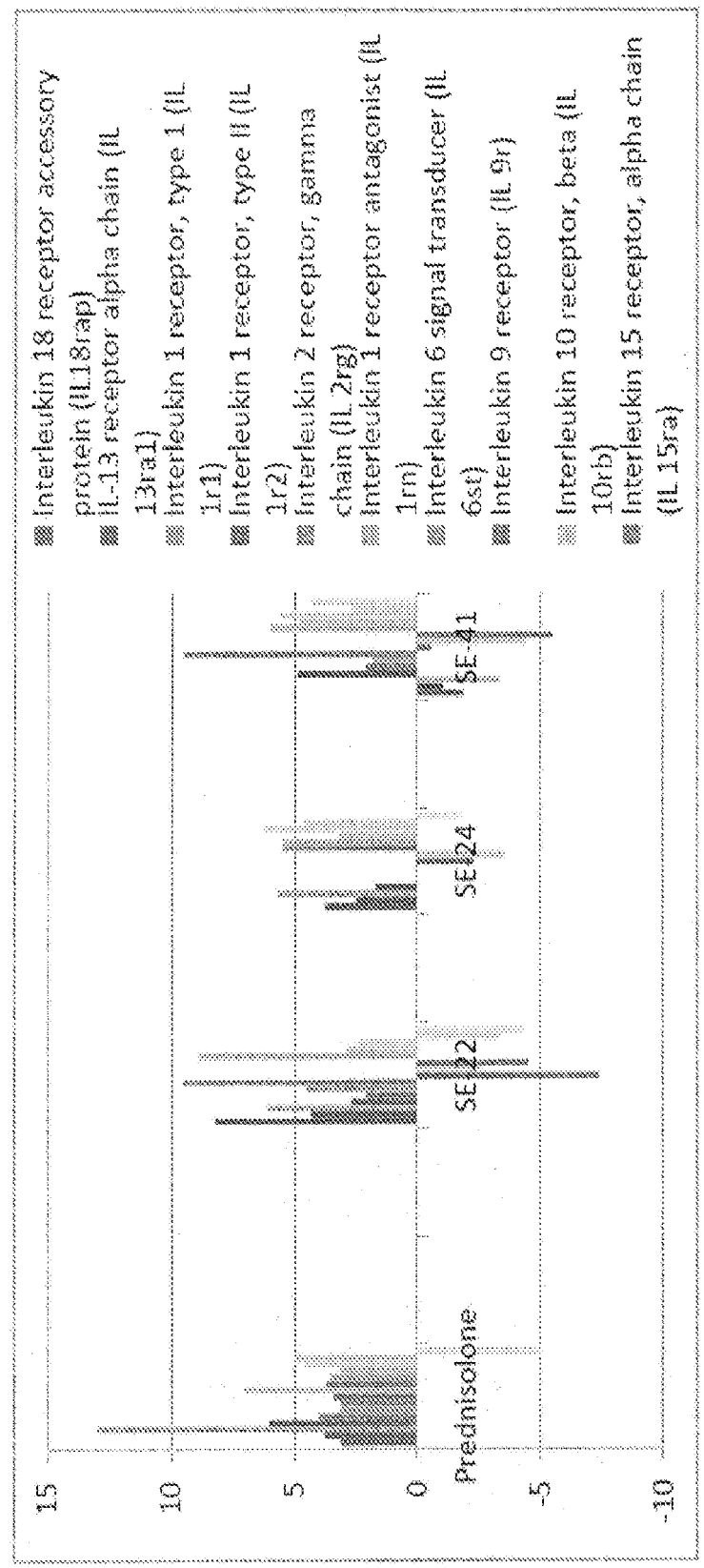
FIG. 10 shows a visual plot of affected interleukins and interleukin receptors.

A number of interleukin receptor and interleukins were affected by all of the compounds tested (prednisolone, SE-22, SE-24 and SE-41). Interleukins promote the development and differentiation of T-, B- and hematopoietic cells. In this series of assays the key interleukins affected are shown below. The majority of interleukins are synthesized by helper CD4+ T lymphocytes, as well as through monocytes, macrophages, and endothelial cells. A reference list of this class of affected targets is presented in FIGS. 9A and B. Also, a visual plot of affected interleukins and interleukin receptors is presented in FIG. 10.

The protein encoded by interleukin-1 receptor, type 1 gene is a cytokine receptor that belongs to the interleukin-1 receptor family. This protein binds interleukin alpha (IL1A), interleukin beta (IL1B), and interleukin 1 receptor, type I (IL1R1/IL1RA), and acts as a decoy receptor that inhibits the activity of its ligands. Interleukin-4 (IL4) is reported to antagonize the activity of interleukin-1 by inducing the expression and release of this cytokine. This gene and three other genes form a cytokine receptor gene cluster on chromosome 2q12. Two alternatively spliced transcript variants encoding the same protein have been reported.

Interleukin-7 receptor. Interleukin-7 receptor has been shown to play a critical role in the development of immune cells called lymphocytes—specifically in a process known as V(D)J recombination. This protein is also found to control the accessibility of a region of the genome that contains the T-cell receptor gamma gene, by STAT5 and histone acetylation. Knockout studies in mice suggest that blocking apoptosis is an essential function of this protein during differentiation and activation of T lymphocytes. Functional defects in this protein may be associated with the pathogenesis of severe combined immunodeficiency (SCID)

Interleukin-1, beta (up-regulated in prednisolone, SE-22, and SE-24; downregulated in SE-41). The protein encoded by this gene is a member of the interleukin 1 cytokine family. This cytokine is produced by activated macrophages as a proprotein, which is proteolytically processed to its active form by caspase 1 (CASP1/ICE). Interleukin-1 beta is an important mediator of the inflammatory response, and is involved in a variety of cellular activities, including cell proliferation, differentiation, and apoptosis. The induction of cyclooxygenase-2 (PTGS2/COX2) by this cytokine in the central nervous system (CNS) is found to contribute to inflammatory pain hypersensitivity. This gene and eight other interleukin 1 family genes form a cytokine gene cluster on chromosome 2.

Interleukin-7 receptor. Interleukin-7 receptor has been shown to play a critical role in the development of immune cells called lymphocytes—specifically in a process known as V(D)J recombination. This protein is also found to control the accessibility of a region of the genome that contains the T-cell receptor gamma gene, by STAT5 and histone acetylation. Knockout studies in mice suggest that blocking apoptosis is an essential function of this protein during differentiation and activation of T lymphocytes. Functional defects in this protein may be associated with the pathogenesis of severe combined immunodeficiency (SCID)

Other key gene responses via compound treatments (prednisolone, SE-22, SE-24 and SE-41).

Insulin induced gene 1. Insulin induced gene 1 encodes an endoplasmic reticulum (ER) membrane protein that plays a critical role in regulating cholesterol concentrations in cells. The protein binds to the sterol-sensing domains of SREBP cleavage-activating protein (SCAP) and HMG CoA reductase, and is essential for the sterol-mediated trafficking of the two proteins. Alternatively spliced transcript variants encoding distinct isoforms have been observed.

Oysterols. Oxysterols regulate cholesterol homeostasis through liver X receptor (LXR) and sterol regulatory element-binding protein (SREBP) mediated signaling pathway. In the gene profiling experiments, prednisolone, SE-22 and SE-24 upregulated the induced insulin gene 1 by over 10-fold. SE-41 was upregulated only by 1.5-fold.

Solute Carrier Family 36 Member 1. The solute carrier (SLC) group of membrane transport proteins include over 300 members organized into 51 families. Most members of the SLC group are located in the cell membrane. The SLC gene nomenclature system was originally proposed by the HUGO Gene Nomenclature Committee (HGNC) and is the basis for the official HGNC names of the genes that encode these transporters. Solutes that are transported by the various SL C group members are extraordinarily diverse and include both charged and uncharged organic molecules as well as inorganic ions and the gas ammonia.

6. Conclusions

Overall, the results indicate that the compounds are bioactive. The gene responses have implications for various cell processes (cell differentiation, immune cell and/or immune response, cell adhesion, lipid metabolism, nuclear hormone receptor activation, transcription and translation modification).

The invention claimed is:
1. A drug conjugate of formula (1),

D-L-P (I), wherein
D is prednisone, prednisolone, methylprednisolone;
L is one or more units of triethylene glycol or succinic acid, or a combination thereof; and,
P is a plant steroid selected from the group consisting of stigmasterol, β-sitosterol, campesterol, brassicasterol, stigmastanol, sitostanol, campestanol, brassicastanol, 24(S),25-epoxycholesterol, and 5-6-epoxycampesterol.
2. The drug conjugate of claim 1, selected from the group consisting of:
prednisolone stigmasterol succinate; and
prednisolone stigmasteroltrisethyleneglycol acetate.
3. The drug conjugate of claim 1, wherein formula (I) is prednisolone stigmasteroltrisethyleneglycolalcohol succinate (formula (10)):

(1o)

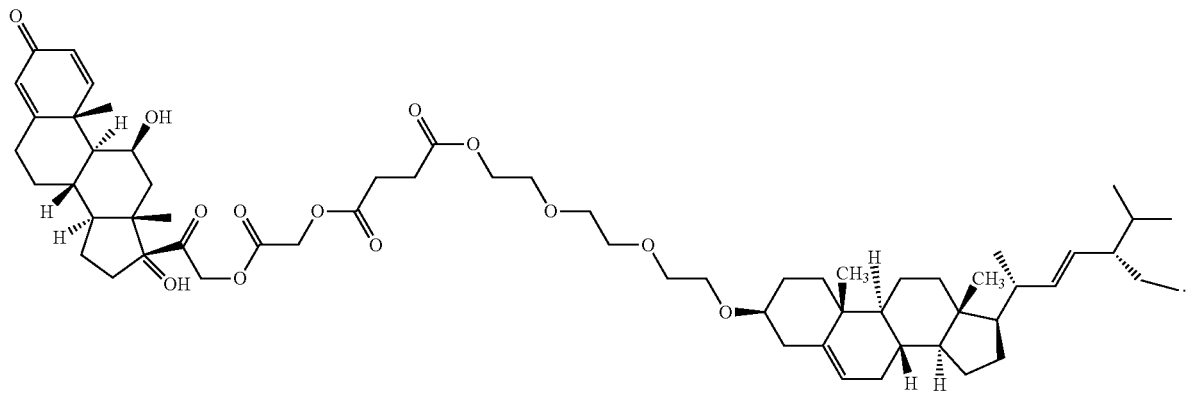

4. The drug conjugate of claim 1, wherein L is a combination of units of triethylene glycol and succinic acid.

5. The drug conjugate of claim 4, wherein P is stigmasterol.

6. The drug conjugate of claim 1, wherein D is prednisolone.

7. The drug conjugate of claim 6, wherein P is stigmasterol.

8. A method for treating a gastro-intestinal disease or an inflammatory condition, comprising administering the drug conjugate of claim 1 to a mammal in need thereof wherein the gastro-intestinal disease or inflammatory condition is selected from the croup consisting of inflammatory bowel disease, celiac disease, inflammatory bowel syndrome, Crohn's disease and ulcerative colitis.

9. The drug conjugate of claim 1, wherein P is stigmasterol.

10. The method of claim 8, wherein the drug conjugate is prednisolone stigmasteroltrisethyleneglycolalcohol succinate (formula (10)):

(1o)

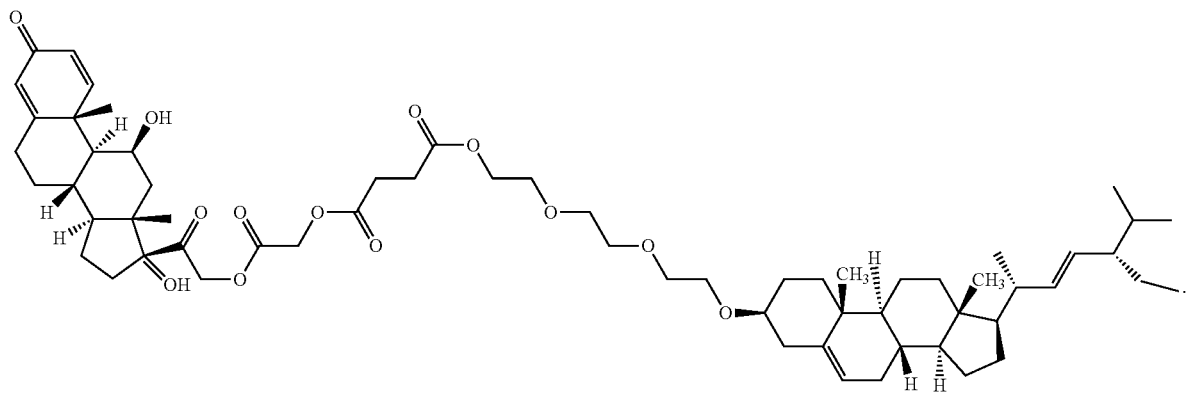

11. The method of claim 10, wherein the gastro-intestinal disease or inflammatory condition is selected from the group consisting of inflammatory bowel disease and celiac disease.

* * * * *

UNITED STATES PATENT AND TRADEMARK OFFICE
CERTIFICATE OF CORRECTION

PATENT NO. : 10,086,082 B2
APPLICATION NO. : 14/345028
DATED : October 2, 2018
INVENTOR(S) : Michael Davidson et al.

Page 1 of 1

It is certified that error appears in the above-identified patent and that said Letters Patent is hereby corrected as shown below:

In the Claims

Claim 1, Column 26, Line 49, please delete "(1)" and insert --(I)--.

Claim 3, Column 26, Line 67, please delete "(formula (10))" and insert --(formula (1o))--.

Claim 3, Column 27, Line 1, formula (1o), that portion of the formula reading:

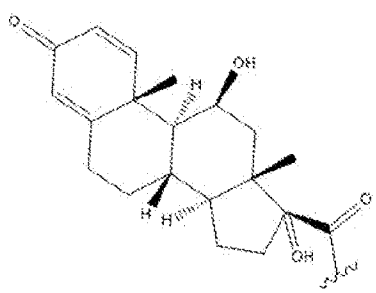     should be changed to     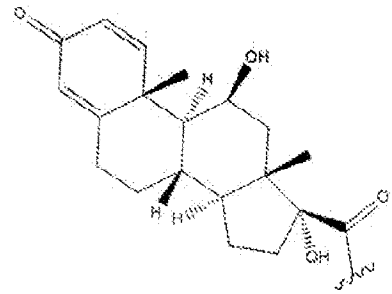

Claim 8, Column 28, Line 23, please delete "croup" and insert --group--.

Claim 10, Column 28, Line 30, please delete "(formula (10))" and insert --(formula (1o))--;
Column 28, Line 31, formula (1o), that portion of the formula read:

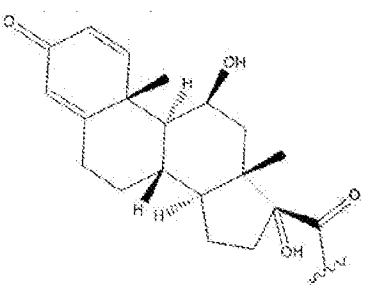     should be changed to     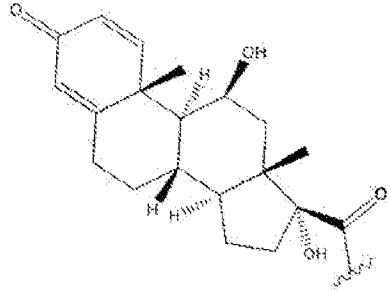

Signed and Sealed this
Twentieth Day of November, 2018

Andrei Iancu
*Director of the United States Patent and Trademark Office*